(12) United States Patent
Roediger et al.

(10) Patent No.: US 11,332,720 B2
(45) Date of Patent: May 17, 2022

(54) MURINE PARVOVIRUS AND USES THEREOF

(71) Applicants: CENTENARY INSTITUTE OF CANCER MEDICINE AND CELL BIOLOGY, Camperdown (AU); UNIVERSITY OF SYDNEY, Sydney (AU)

(72) Inventors: Ben Roediger, Annandale (AU); Wolfgang Weninger, Glebe (AU); Shweta Tikoo, Camperdown (AU)

(73) Assignees: Centenary Institute of Cancer Medicine and Cell Biology, Camperdown (AU); University of Sydney, Sydney (AU)

( * ) Notice: Subject to any disclaimer, the term of this patent is extended or adjusted under 35 U.S.C. 154(b) by 16 days.

(21) Appl. No.: 16/616,212

(22) PCT Filed: May 25, 2018

(86) PCT No.: PCT/AU2018/050505
§ 371 (c)(1),
(2) Date: Nov. 22, 2019

(87) PCT Pub. No.: WO2018/213888
PCT Pub. Date: Nov. 29, 2018

(65) Prior Publication Data
US 2020/0140829 A1 May 7, 2020

(30) Foreign Application Priority Data
May 25, 2017 (AU) ................................. 2017901985

(51) Int. Cl.
*C12N 7/00* (2006.01)
*C12N 15/86* (2006.01)
(Continued)

(52) U.S. Cl.
CPC ............ *C12N 7/00* (2013.01); *A01K 67/0273* (2013.01); *C12N 15/86* (2013.01);
(Continued)

(58) Field of Classification Search
None
See application file for complete search history.

(56) References Cited

U.S. PATENT DOCUMENTS

2020/0140829 A1* 5/2020 Roediger ............ A01K 67/0273

OTHER PUBLICATIONS

Roediger et al. (2018. Cell; 175: 530-543).*
(Continued)

*Primary Examiner* — Shanon A. Foley
(74) *Attorney, Agent, or Firm* — Thompson Coburn LLP; William A. Holtz

(57) ABSTRACT

The present disclosure relates to a novel murine parvovirus, sequences encoded thereby, and applications therefor. In one embodiment the disclosure provides a method for detecting the presence of a parvovirus in a sample, comprising detecting one or more nucleic acids or polypeptides derived from the parvovirus, or antibodies against the parvovirus, in the sample. Also provided are vectors and host cells comprising sequences encoded by the parvovirus and related sequences. Also provided are animal models of kidney disease associated with infection by the parvovirus.

7 Claims, 13 Drawing Sheets

Specification includes a Sequence Listing.

(51) Int. Cl.
*G01N 33/569* (2006.01)
*A01K 67/027* (2006.01)

(52) U.S. Cl.
CPC .................. *G01N 33/56983* (2013.01); *A01K 2267/0337* (2013.01); *C12N 2750/14021* (2013.01); *C12N 2750/14023* (2013.01); *C12N 2750/14032* (2013.01); *C12N 2750/14033* (2013.01); *G01N 2333/015* (2013.01)

(56) References Cited

OTHER PUBLICATIONS

Genbank Accession KX907333, Dec. 16,2 016, 3 pages.
Genbank Accession A0A1L4AJD0_9VIRU, Mar. 15, 2017, 1 page.
Genbank Accession A0A1L4AJD9_9VIRU, Mar. 15, 2017, 1 page.
Genbank Accession MF175078, May 2, 2018, 3 pages.
Genbank Accession AWB14584, May 2, 2018, 2 pages.
Genbank Accession AWB14583, May 2, 2018, 2 pages.
Roediger et al., "An Atypical Parvovirus Drives Chronic Tubulointerstitial Nephropathy and Kidney Fibrosis", Cell, 2018, pp. 530-543, vol. 175.
Souza et al., "Chapparvoviruses occur in at least three vertebrate classes and have a broad biogeographic distribution", Journal of General Virology, 2017, pp. 225-229, vol. 98.
Williams et al., "Viral Diversity of House Mice in New York City", mBIO, 2018, pp. 1-17, vol. 9, Issue 2.
Genbank Accession KX907333, Dec. 13, 2016, 3 pages.
Genbank Accession MF175078, Apr. 25, 2018, 2 pages.
Genbank Accession AWB14583, Apr. 25, 2018, 2 pages.
Genbank Accession AWB14584, Apr. 25, 2018, 1 page.

* cited by examiner

FIGURE 5
A
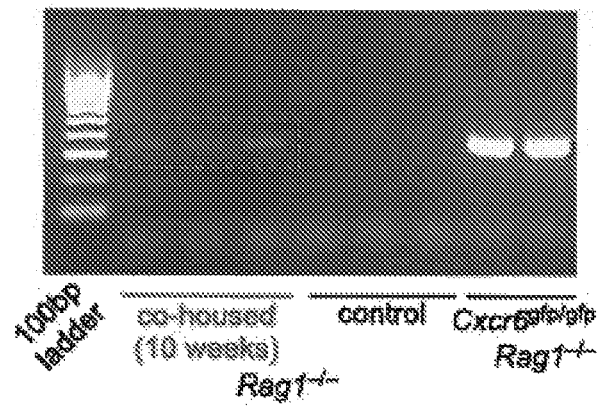
B
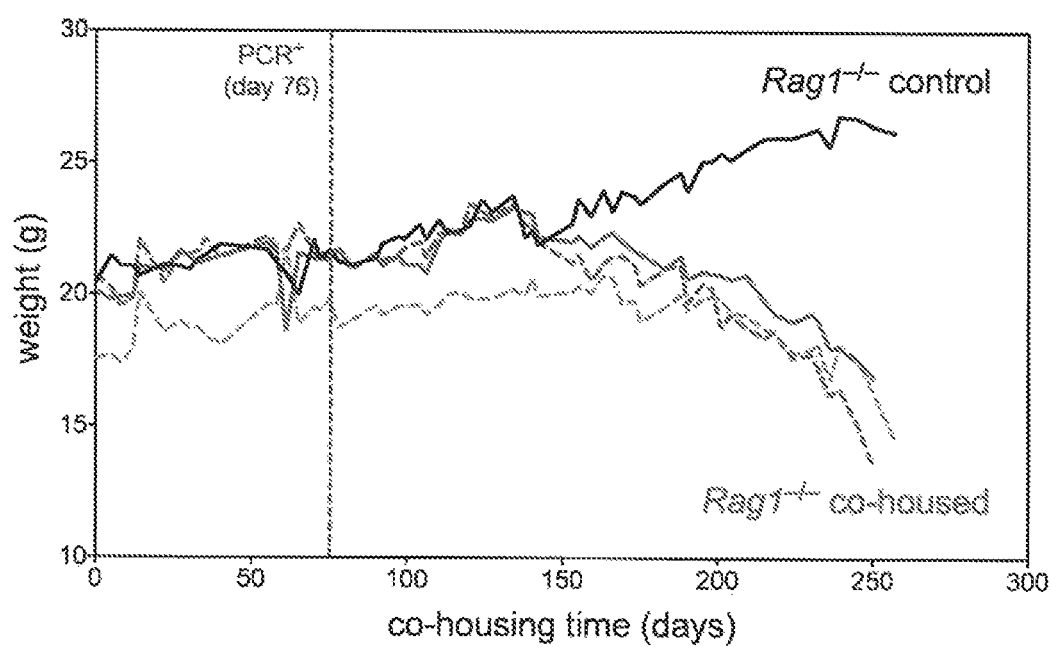

FIGURE 6

FIGURE 8
A
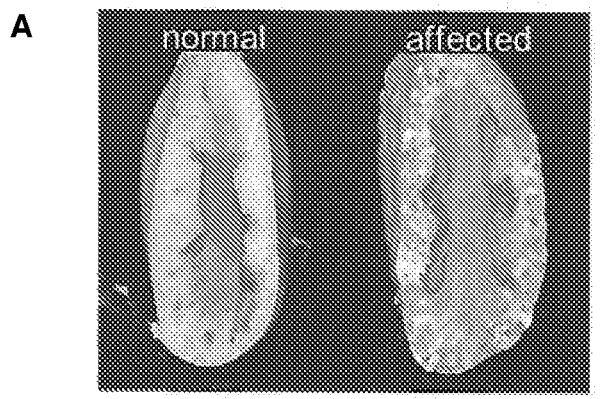
B
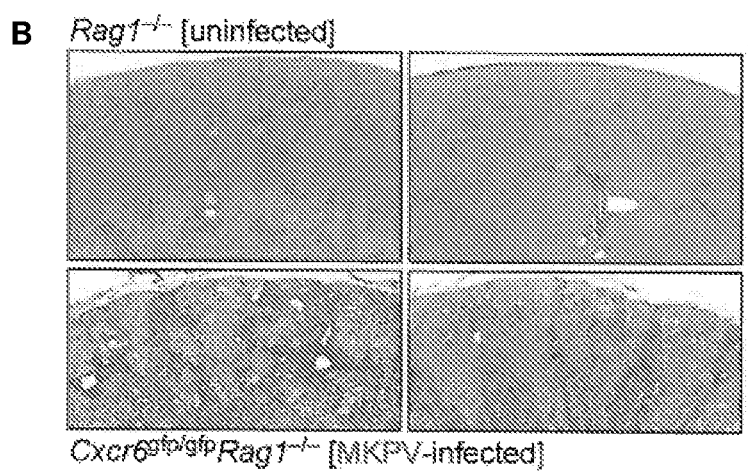
C
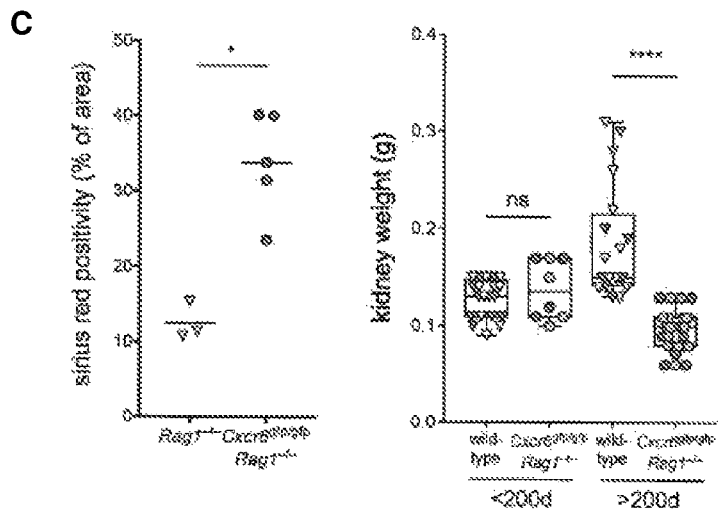

FIGURE 11
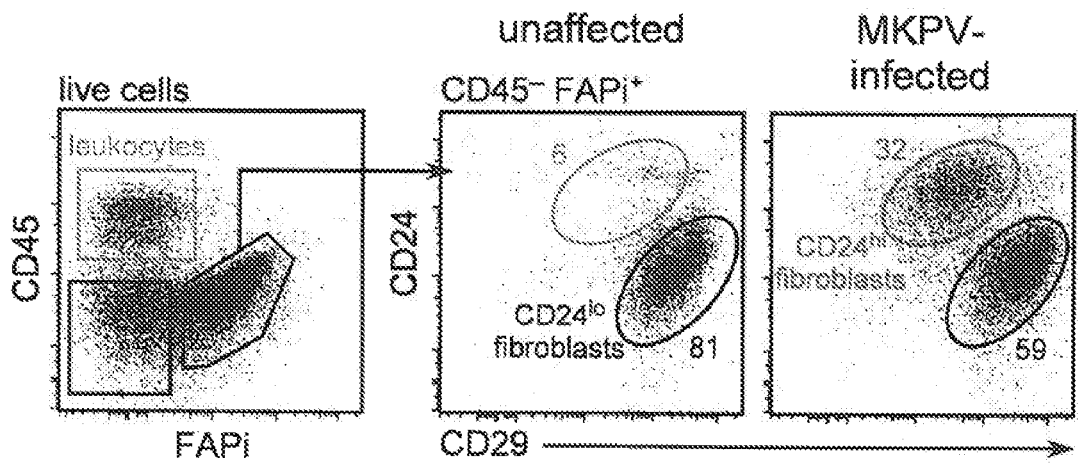
FIGURE 12
A
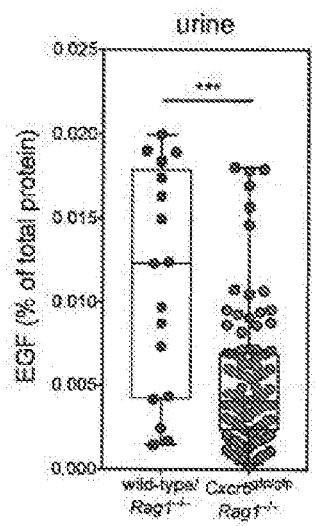
B
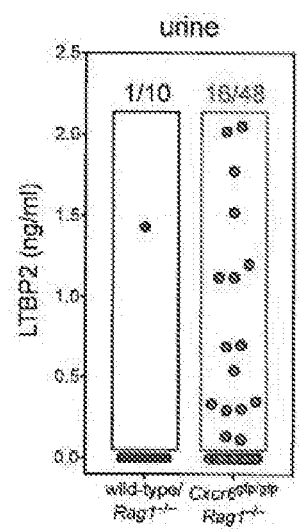

FIGURE 16

MKPV NS1 (SEQ ID NO:4)
Matched peptides shown in bold underine.
```
1   MQAQMERARR SLSALRRYWW GGNACHQLSE ESEIISPENL KQIMLNWDSR
51  VWQACVLGIW DTVPVRDPRP YCFLLTNIPS VKKWLICAEE DSNEQTHIHL
101 LALTSQRSDA FKRTLEKTWK QVAIVAMSDI EEPDPTLEIV KCQKCHKPSS
151 LLAYMAKDPH WIAANDMQTL GIFESVYAHD WGQRFREKQT LDKAKKTDPT
201 TSQMHTITAE ITEVIMQHNC KSVEDCMKAA PTVIAKHLHR AGLGTIIQNC
251 ISWVTATGGG WSLPSIGAKH PPEPEAIHTI LLHQGISPAD FDPIFYKWLA
301 KEETKKNTLV LWGPSNTGKS AFISGLKTCT NWGEVVNSNT FAFEALINAQ
351 LGVWEEPLIS PELAEKAKQI FEGMETSIPV KYRKPVKLPR IPIIITTNHA
401 PWRFCTKEEE MFRNRMYIFT WSQNMHDTPF ICRASEYSCQ CRVCQTSRGG
451 QACAGGQSAG SLQRKEQSVS ELVQPEPSSS YVSTRSLPVS REETPLPAAE
501 GLGSHHQRHC SSPGGESIER THSPRPSCST GSSTSDSLRP SGEHRSSDPG
551 AGISCSFSGS LECVESPLSG GDDGDDLPRD RMGEPTSPDS STGSSDISRP
601 RGKRRHSQEM VVLGETQSKK TRDQVSTAVT GMGRDLGTLN IPTRAQWFTY
651 LSYLQKHYG
```

MKPV VP1 (SEQ ID NO:8)
Matched peptides shown in bold underline.
```
1   MAEDVTFHNT YMVYWKNQPF IYPNTNINPP NAHTMSAGAI NTGWHIIPTI
51  LWKHFLTPKQ WTEFTINYEA YTVKGYSCTI YNPIPMTQQL AIQGTTAFTA
101 FNNTIYTLGA QDDLYETAYH NWYSDDSTGD YKAFNLSFKE GQYKNLSGSW
151 KKTIWPIYSW RTENARNASS STYSYLNGID SYAVWPRTKD KELIPTGVFW
201 DPLNDANGIL ELRPGKNSMS FSWEQHPCDE NKWFNIDQIA KWFPYTVDTP
251 YLNPQTYGPP GSYKLYGEDD PDQLTTPSSW TAYSAKNDYT IPNLLDMPIV
301 PMQWFWQEIQ KSIAEVPDVK KPMLYWAGTE YECYKYGPTQ CFLKGIPLFD
351 DNDTHVATTT QGCFRISLHL AGKKRRSRIY APTWGPLSWR QCYATDTPFA
401 PSMVRYRTGG ARRTWTNINR DAEGVHKDFH YREDPYDITS TVPDTRGTAT
451 VTDSKATMHP YEQAASGMYL NHKEMRQVRA AAEATRSQPA VAMQTQ
```

MURINE PARVOVIRUS AND USES THEREOF

CROSS-REFERENCE TO RELATED APPLICATIONS

This patent application is a national phase application of PCT/AU2018/050505, filed on May 25, 2018, claiming the benefit of Australian Patent Application No. 2017901985 filed May 25, 2017, both of which are incorporated herein by reference in their entireties.

REFERENCE TO SEQUENCE LISTING SUBMITTED ELECTRONICALLY

The content of the electronically submitted sequence listing in the ASCII text file (Name: Substitute Sequence Listing MKPV_ST25.txt; Size: 59,229 bytes; and Date of Creation: Dec. 10, 2021) filed with the application is incorporated herein by reference in its entirety.

FIELD OF THE ART

The present disclosure relates generally to a novel parvovirus that infects mice, typically infecting cells of the kidneys, and to uses of the parvovirus as an animal model of chronic kidney disease, in the screening and identification of therapeutic agents for the treatment of chronic kidney disease, in the development of viral vectors, for the identification of the presence of the virus in animals, and for determining the history of exposure of an animal to the virus.

BACKGROUND

Chronic kidney disease, defined as kidney dysfunction of at least three months duration, affects 3-18% of adults globally. Chronic kidney disease arises from a range of conditions that alter the structure and function of the kidneys, including diabetes mellitus, hypertension, glomerulonephritis and exposure to certain drugs. Irrespective of the underlying source of injury, renal failure in chronic kidney disease occurs as a result of irreversible fibrosis ('scarring') of the kidney. The development of effective interventions for renal fibrosis and failure has been hindered by the paucity of animal models of chronic kidney disease.

Viral infections can underlie kidney fibrosis, for example in the setting of kidney transplantation, in which immunosuppression can result in the reactivation of latent viruses within the donor allograft. Viral reactivation may lead to parenchymal cell damage, reactive tissue fibrosis, compromised renal function and eventual loss of the transplant. Polyomavirus-associated nephropathy has emerged as a significant cause of morbidity in transplant patients. The most common infectious agent in this regard is BK virus, a small single-strand DNA virus that propagates within the tubular epithelial cells of the donor kidney. The resultant tubular damage provokes fibrosis and significantly compromises renal function leading to graft loss. Other viruses, such as adenovirus, have also been associated with kidney failure in transplanted patients.

Inclusion body nephritis (tubulointerstitial nephritis) is an idiopathic condition that has been observed in both immunocompetent and immunocompromised mice. Inclusion body nephritis was described by mouse pathologists over 30 years ago. In immunodeficient recombination activating gene (RAG) knockout animals, this disease causes renal failure between 170 and 400 days of life (5-13 months, occasionally younger). The pathological effects of inclusion body nephritis have been previously described in multiple laboratories globally and its high mortality rate in immunocompromised mice makes it particularly devastating to research colonies. While the cause of inclusion body nephritis has remained elusive, it is widely believed to be a degenerative disease, however there is currently no method available to predict or determine susceptible individuals. Methods of detection of the disease in laboratory animals are essential for reliable and reproducible experimentation and to prevent morbidity and mortality of animals. Additionally, due to the chronic and fibrotic state of animals with inclusion body nephritis, such animals may provide a model for human chronic kidney disease.

SUMMARY OF THE DISCLOSURE

Using a metagenomics approach, the present inventors have identified a causative pathogen of murine inclusion body nephritis as a novel virus, termed mouse kidney parvovirus (MKPV), belonging to a previously unclassified genus of *parvoviridae*. Based on clinical course, histopathologic features and measurements of biomarkers as exemplified herein, MKPV infection represents a model for chronic tubulointerstitial nephritis in humans. The present disclosure also provides tools deriving from the identification of MKPV, including for the identification of the presence of this virus in mice and other animal species, and for determining the history of exposure to this virus in mice and other animal species. Also provided are uses of MKPV as an animal model of chronic kidney disease, in the screening and identification of therapeutic agents for the treatment of chronic kidney disease, and in the development of viral vectors that use the capsid sequence of, or derived from, MKPV.

According to a first aspect of the present disclosure there is provided a method for detecting the presence of a parvovirus in a sample, comprising detecting one or more nucleic acids or polypeptides derived from the parvovirus, or antibodies against the parvovirus, in the sample, wherein the parvovirus comprises:

(i) a gene encoding a non-structural (NS1) protein comprising the amino acid sequence set forth in SEQ ID NO:4, or an amino acid sequence comprising at least about 80% amino acid sequence identity thereto;

(ii) a gene encoding a non-structural (NS2) protein comprising the amino acid sequence set forth in any one of SEQ ID NOs:5 to 7, or an amino acid sequence comprising at least about 80% amino acid sequence identity thereto;

(iii) a gene encoding a capsid protein (VP1) comprising the amino acid sequence set forth in SEQ ID NO:8, or an amino acid sequence comprising at least about 80% amino acid sequence identity thereto; or (iv) the nucleotide sequence set forth in SEQ ID NO:3 or a nucleotide sequence comprising at least about 70% sequence identity thereto.

The method may detect the presence of the parvovirus in an environment, an active or latent infection of an animal with the parvovirus or the history of exposure of an animal to the parvovirus.

In an embodiment, the method comprises detecting one or more nucleic acids derived from the parvovirus in the sample. The method may comprise isolating one or more nucleic acids from the sample, amplifying at least one of the nucleic acids; and analyzing the amplified nucleic acids to identify the presence of the parvovirus. The method may comprise polymerase chain reaction-based amplification and analysis. The sample may be a biological sample from an organism or may be an environmental sample. The environmental sample may comprise, for example, environmental air dust.

In an alternative embodiment, the method comprises one or more serological tests or immunoassays to detect one or more antibodies against the parvovirus in the sample.

According to a second aspect, the present disclosure provides an isolated murine parvovirus comprising a gene encoding a non-structural (NS) protein comprising the amino acid sequence set forth in any one of SEQ ID NOs:4 to 7, or an amino acid sequence comprising at least about 80% amino acid sequence identity thereto, wherein said parvovirus is capable of infecting murine kidney cells and causing murine kidney disease.

In one embodiment the parvovirus comprises a gene encoding an NS1 protein comprising the amino acid sequence set forth in SEQ ID NO:4 or an amino acid sequence comprising at least about 80% amino acid sequence identity thereto. The NS1 gene may comprise the nucleotide sequence set forth in SEQ ID NO:9 or a nucleotide sequence at least about 90% identical thereto.

In another embodiment the parvovirus comprises a gene encoding a NS2 protein comprising the amino acid sequence set forth in any one of SEQ ID NOs:5 to 7, or an amino acid sequence comprising at least about 80% amino acid sequence identity thereto. The NS2 gene may comprise the nucleotide sequence set forth in any one of SEQ ID NOs:10 to 12 or a nucleotide sequence at least about 90% identical thereto.

Also provided is an isolated NS1 polypeptide comprising the amino acid sequence set forth in SEQ ID NO:4 or an amino acid sequence comprising at least about 80% amino acid sequence identity to SEQ ID NO:4. Also provided is an isolated NS2 polypeptide comprising the amino acid sequence set forth in any one of SEQ ID NOs:5 to 7 or an amino acid sequence comprising at least about 80% amino acid sequence identity thereto.

According to a third aspect, the present disclosure provides an isolated murine parvovirus comprising a gene encoding a capsid protein VP1 comprising the amino acid sequence set forth in SEQ ID NO:8 or an amino acid sequence comprising at least about 80% amino acid sequence identity to SEQ ID NO:8, wherein said parvovirus is capable of infecting murine kidney cells and causing murine kidney disease.

Also provided is an isolated VP1 polypeptide comprising the amino acid sequence set forth in SEQ ID NO:8 or an amino acid sequence comprising at least about 80% amino acid sequence identity to SEQ ID NO:8. The VP1 gene may comprise the nucleotide sequence set forth in SEQ ID NO:13 or a nucleotide sequence at least about 90% identical thereto.

According to a fourth aspect, the present disclosure provides an isolated murine parvovirus comprising the nucleotide sequence set forth in SEQ ID NO:3 or a nucleotide sequence comprising at least about 70% sequence identity to SEQ ID NO:3, wherein said parvovirus is capable of infecting murine kidney cells and causing murine kidney disease.

In accordance with embodiments of the above aspects, the parvovirus infects mouse kidney cells and causes kidney disease in mice. The murine kidney disease may be a chronic kidney disease. The kidney disease may comprise, or be characterized by, inclusion body nephritis (tubulointerstitial nephritis) or kidney fibrosis.

According to a fifth aspect, the present disclosure provides an isolated host cell infected with the parvovirus of the second, third or fourth aspect, or a host cell comprising a vector comprising one or more nucleotide sequences of said parvovirus.

According to a sixth aspect, the present disclosure provides a murine animal for use as an animal model of kidney disease, wherein the murine animal is infected with the parvovirus as defined in the second, third or fourth aspect.

Typically the animal model displays one or more symptoms of, or histopathologic features characteristic of, or associated with, the kidney disease. The kidney disease may be a chronic kidney disease of humans, optionally immunocompromised humans. The kidney disease may comprise, or be characterized by, human tubulointerstitial nephritis or kidney fibrosis. Symptoms and histopathologic features characteristic of, or associated with, the kidney disease may include tubular epithelial cells with enlarged nuclei (karyomegaly), the formation of eosinophilic intranuclear inclusion bodies in tubular epithelial cells, fibrosis, reduced renal mass, and kidney dysfunction (as determined, for example, by reduced proteinuria, weight loss and/or reduced urinary creatinine levels).

The animal model may be used in the study of pathophysiological features and progression of kidney disease, optionally human kidney disease, including, for example, disease characterized by, or associated with, tubulointerstitial nephritis or kidney fibrosis.

The animal model may be used in the screening of candidate compounds for use in the treatment of kidney disease.

The animal model may be used in the identification of biomarkers of kidney disease.

According to a seventh aspect, the present disclosure provides a method for screening a candidate compound for use in the treatment of kidney disease, comprising: i) administering the candidate compound to a murine animal model infected with the parvovirus as defined in the second, third or fourth aspect, which animal model displays one or more symptoms of, or histopathologic features characteristic of, or associated with, the kidney disease; ii) characterizing the phenotype of the murine animal model after administration of the candidate compound; and iii) selecting the candidate compound that reverses or delays one or more symptoms, or histopathologic features characteristic of or associated with, the kidney disease, as a compound for use in the treatment of kidney disease.

The kidney disease may be a chronic kidney disease of humans, optionally immunocompromised humans. The kidney disease may comprise, or be characterized by, human tubulointerstitial nephritis or kidney fibrosis. Symptoms and histopathologic features characteristic of, or associated with the kidney disease may include tubular epithelial cells with enlarged nuclei (karyomegaly), the formation of eosinophilic intranuclear inclusion bodies in tubular epithelial cells, fibrosis, reduced renal mass, and kidney dysfunction (as determined, for example, by reduced proteinuria, weight loss and/or reduced urinary creatinine levels).

According to an eighth aspect, the present disclosure provides a method for detecting infection of an animal or cell with the parvovirus as defined in the second, third or fourth aspect, the method comprising contacting a biological sample derived from the animal or cell with one or more oligonucleotides specific for at least one target murine kidney parvovirus nucleic acid sequence under conditions sufficient for amplification of at least one target sequence producing a murine kidney parvovirus amplification product.

The cell may be a cell line, such as an immortalized or other laboratory cell line, or may be derived from an animal. In an embodiment, the animal is a murine laboratory animal. Typically the animal is a mouse. In embodiments, the animal may be immunocompromised or immunodeficient. In exemplary embodiments, the biological sample may comprise urine, serum or one or more tubular epithelial cells isolated from the animal.

The at least one target murine kidney parvovirus nucleic acid sequence may comprise NS1, NS2 or VP1 DNA. The at least one primer may comprise a nucleotide sequence as set forth in SEQ ID NO:1 or SEQ ID NO:2, or a nucleotide sequence having at least about 90% sequence identity to SEQ ID NO:1 or SEQ ID NO:2. Primers may be designed to amplify a region comprising a sequence encoding the NS1 (SEQ ID NO:4), NS2 (SEQ ID NO:5, 6 or 7) or VP1 (SEQ ID NO:8) protein.

According to a ninth aspect, the present disclosure provides the use of the parvovirus as defined in the second, third or fourth aspect, or one or more viral polypeptides derived therefrom, for the identification of antibodies against the parvovirus in a biological sample.

According to a tenth aspect, the present disclosure provides a vector comprising a nucleic acid molecule comprising a nucleotide sequence as set forth in any one of SEQ ID NOs:9 to 13, or a nucleotide sequence at least about 90% identical thereto.

The vector may be selected from among a plasmid, cosmid, phage, transposon and viral vector. In particular embodiments the vector is a viral vector. Optionally, the vector may further comprise one or more heterologous sequences. The vector may be designed for introduction into kidney cells and to direct or facilitate expression of the one or more heterologous sequences in kidney cells.

According to an eleventh aspect, the present disclosure provides a recombinant virus comprising a capsid protein comprising the amino acid sequence set forth in SEQ ID NO:8 or an amino acid sequence comprising at least about 80% amino acid sequence identity to SEQ ID NO:8.

In exemplary embodiments, the recombinant virus further comprises one or more heterologous sequences.

According to a twelfth aspect, the present disclosure provides a method for introducing a heterologous sequence into a host cell, comprising contacting a host cell with a vector according to the tenth aspect, wherein the vector comprises the heterologous sequence, or a recombinant virus according to the twelfth aspect, wherein the recombinant virus comprises the heterologous sequence.

In an exemplary embodiment, the host cell may be a kidney cell.

BRIEF DESCRIPTION OF THE DRAWINGS

Aspects and embodiments of the present disclosure are described herein, by way of non-limiting example only, with reference to the following drawings.

FIG. 5. A. Detection of viral DNA in serum of Rag1$^{-/-}$ mice after co-housing with affected Cxcr6$^{gfp/gfp}$ Rag1$^{-/-}$ mice. B. Transmission of kidney disease in immunodeficient mice. Weight loss kinetics in Rag1$^{-/-}$ mice after co-housing with disease-affected Cxcr6$^{gfp/gfp}$ Rag1$^{-/-}$ mice. Control Rag1$^{-/-}$ littermate shown in black. Representative of 3 independent experiments.

FIG. 6. Parvovirus amino acid sequence comparison. Complete NS1 amino acid comparison between MKPV and selected parvoviruses of low (mouse parvovirus 1) and high (porcine parvovirus 7, rat parvovirus 2, eidolon helvum parvovirus 2) similarity.

FIG. 8. Chronic kidney disease in MKPV-infected mice. A. Iodine-enhanced micro-computed tomography reconstructions of normal (left) and disease-affected (right) kidneys. B. Sirius Red staining of kidneys from uninfected Rag1$^{-/-}$ mice (top) and MKPV-infected Cxcr6$^{gfp/gfp}$ Rag1$^{-/-}$ mice (bottom). Right: Quantification of Sirius Red staining (n=3 uninfected mice, n=5 MKPV-infected mice). *P=0.0345. C. Kidney weights from wild-type and uninfected Rag1$^{-/-}$ mice and MKPV-infected Cxcr6$^{gfp/gfp}$ Rag1$^{-/-}$ mice, stratified according to age. Both left (pale grey triangles and orange circles) and right (dark grey triangles and red circles) kidneys have been included. ***P<0.0001.

FIG. 11. Myofibroblast conversion in MKPV-infection. Left: Flow cytometry dotplot of CD45$^+$ leukocytes and FAP$^+$ fibroblasts isolated from normal kidneys. Middle and right: Flow cytometry dotplots depicting CD24 (heat-stable antigen) and CD29 (β1 integrin) expression by FAP$^+$ fibroblasts isolated from unaffected (middle) and MKPV-infected (right) kidneys. CD24$^+$ CD29$^{lo}$ myofibroblasts are gated in red. Representative of 2 independent experiments.

FIG. 12. Urinary epidermal growth factor (EGF) (A) and latent TGFβ-binding protein 2 (LTBP2) (B) levels in uninfected wild-type and Rag1$^{-/-}$ mice (black circles; left hand side) and MKPV-infected Cxcr6$^{gfp/gfp}$ Rag1$^{-/-}$ mice (red circles; right hand side). ***P=0.0004.

FIG. 16. MKPV proteins in disease-affected kidneys. Summaries of mass spectrometry assessment of MKPV-infected kidneys of a Cxcr6$^{gfp/gfp}$ Rag1$^{-/-}$ mouse. Kidney protein was extracted using RIPA (radioimmunoprecipitation assay) lysis and extraction buffer, followed by digestion with trypsin. Detected peptides shown in bold underline. These peptides were not detected in kidneys from an unaffected Rag1$^{-/-}$ mouse.

Figure 1:
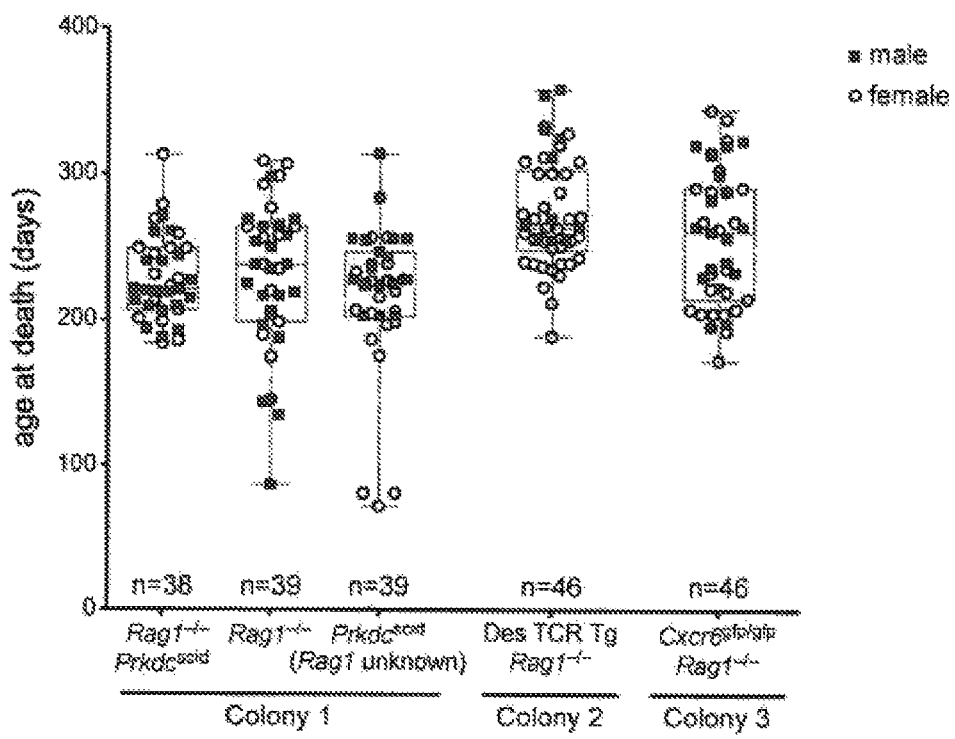
FIG. 1. Renal disease in immunodeficient mice. Age of death data for necropsy-confirmed renal disease in three separate colonies of immunodeficient mice.
Figure 2:
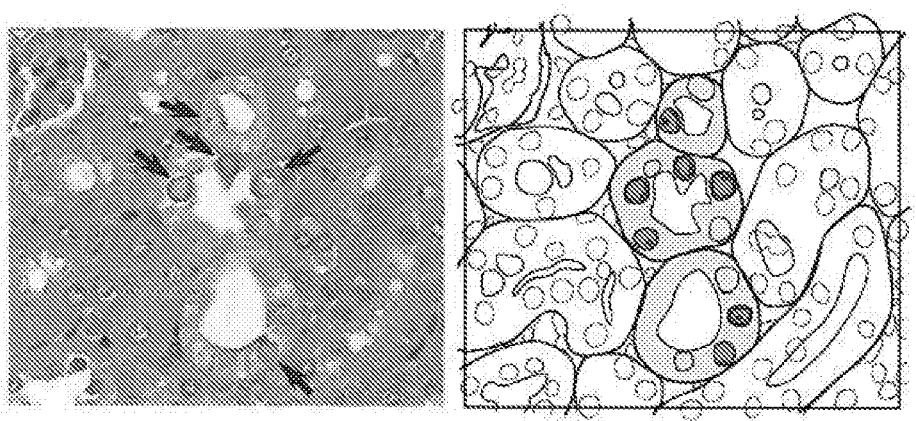
FIG. 2. Histopathology of disease-affected kidney. Arrows indicate chromatin clearing and nuclear inclusion bodies.

Nucleotide and amino acid sequences referred to herein are included in a Sequence Listing generated using PatentIn 3.5. SEQ ID NOs: 1 and 2 represent oligonucleotide primer sequences exemplified herein. The complete nucleotide sequence of the MKPV virus the subject of the present disclosure is provided in SEQ ID NO:3. The amino acid sequences of the NS1 and VP1 proteins encoded by MKPV are provided in SEQ ID NOs:4 and 8, respectively. Sequences of three variants of the NS2 protein encoded by MKPV are provided in SEQ ID NOs:5 to 7. The nucleotide sequences of genes encoding NS1, NS2 and VP1 proteins encoded by MKPV are provided in SEQ ID NOs:9 (NS1), SEQ ID NOs:10-12 (three variants of NS2) and SEQ ID NO:13 (VP1). The amino acid of an exemplary peptide sequence derived from MKPV VP1 is shown in SEQ ID NO:14.

DETAILED DESCRIPTION

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

The articles "a" and "an" are used herein to refer to one or to more than one (i.e., to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

The term "host cell" refers to a cell, typically a mammalian cell, that has introduced into it exogenous DNA, such as a vector. The term includes the progeny of the original cell into which the exogenous DNA has been introduced. Thus, a "host cell" as used herein generally refers to a cell that has been transfected or transduced with exogenous DNA.

As used herein, "isolated" with reference to a nucleic acid molecule means that the nucleic acid molecule is substantially free of cellular material or other contaminating proteins from the cells from which the nucleic acid molecule is derived, or substantially free from chemical precursors or other chemicals when chemically synthesized.

A "heterologous sequence" as used herein refers to nucleic acid sequence present in a polynucleotide, vector, or host cell that is not naturally found in the polynucleotide, vector, or host cell or is not naturally found at the position that it is at in the polynucleotide, vector, or host cell, i.e. is non-native. A "heterologous sequence" can encode a peptide or polypeptide, or a polynucleotide that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur.

In the context of the present specification, the terms "protein" and "polypeptide" may be used interchangeably herein.

As used herein, the terms "treating", "treatment" and the like refer to any and all applications which remedy, or otherwise hinder, retard, or reverse the progression of, a disease or at least one symptom of a disease, including reducing the severity of a disease.

The present disclosure is predicated on the inventors' identification of a novel murine parvovirus, termed mouse kidney parvovirus (MKPV), which infects kidney cells of mice and causes, particularly in immunocompromised mice, symptoms and histopathological features that are hallmarks of tubulointerstitial nephritis and kidney fibrosis.

Chronic kidney disease is characterized by long-term structural and functional abnormalities. Currently used animal models of kidney fibrosis and chronic kidney disease mostly rely on the generation of relatively short-term injuries, which fail to recapitulate the chronic nature of fibrotic disease in humans. In addition, there are few models that allow for the investigation of viral reactivation within kidneys. As such, MKPV infection represents a novel tool for dissecting the pathophysiology of tubulointerstitial nephritis and kidney fibrosis, with similarities to polyomavirus-associated nephropathy. The utility of investigating MKPV infection is corroborated by the fact that, as exemplified herein, the inventors have identified kidney damage biomarkers shared with humans that correlate with disease stage in infected mice. Exploiting this infection system will facilitate the dissection of the pathogenesis of fibrotic kidney changes as well as the development of new biomarkers and therapeutic targets for kidney damage and fibrosis.

MKPV

Provided herein is an isolated murine parvovirus comprising a gene encoding a non-structural protein 1 (NS1) comprising the amino acid sequence set forth in SEQ ID NO:4 or an amino acid sequence comprising at least about 80% amino acid sequence identity to SEQ ID NO:4, wherein said parvovirus is capable of infecting murine kidney cells and causing murine kidney disease.

Also provided herein is an isolated murine parvovirus comprising a gene encoding a non-structural protein 2 (NS2) comprising the amino acid sequence set forth in SEQ ID NO:5, 6 or 7 or an amino acid sequence comprising at least about 80% amino acid sequence identity thereto, wherein said parvovirus is capable of infecting murine kidney cells and causing murine kidney disease.

Also provided herein is an isolated murine parvovirus comprising a gene encoding a capsid protein VP1 comprising the amino acid sequence set forth in SEQ ID NO:8 or an amino acid sequence comprising at least about 80% amino acid sequence identity to SEQ ID NO:8, wherein said parvovirus is capable of infecting murine kidney cells and causing murine kidney disease.

The parvovirus may encode a NS1, NS2 or VP1 protein having at least about 80%, 81%, 82%, 83%, 84%, 85%, 86%, 87%, 88%, 89%, 90%, 91%, 92%, 93%, 94%, 95%, 96%, 97%, 98% or 99% amino acid sequence identity to any one of SEQ ID NOs:4 to 8.

Thus, also provided are NS1 polypeptides comprising an amino acid sequence as set forth in SEQ ID NO:4, or having at least about 80%, 81%, 82%, 83%, 84%, 85%, 86%, 87%, 88%, 89%, 90%, 91%, 92%, 93%, 94%, 95%, 96%, 97%, 98% or 99% amino acid sequence identity to SEQ ID NO:4.

Also provided are NS2 polypeptides comprising an amino acid sequence as set forth in SEQ ID NO:5, 6 or 7, or having at least about 80%, 81%, 82%, 83%, 84%, 85%, 86%, 87%, 88%, 89%, 90%, 91%, 92%, 93%, 94%, 95%, 96%, 97%, 98% or 99% amino acid sequence identity to SEQ ID NO:5, 6 or 7.

Also provided are VP1 capsid polypeptides comprising an amino acid sequence as set forth in SEQ ID NO:8, or having at least about 80%, 81%, 82%, 83%, 84%, 85%, 86%, 87%, 88%, 89%, 90%, 91%, 92%, 93%, 94%, 95%, 96%, 97%, 98% or 99% amino acid sequence identity to SEQ ID NO:8.

Also provided are isolated nucleic acid molecules encoding the NS1, NS2 or VP1 polypeptides described herein. For example, the nucleic acid molecule encoding NS1 may comprise a nucleotide sequence as set forth in SEQ ID NO:9 or a sequence having at least or about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:9. For example, the nucleic acid molecule encoding NS2 may comprise a nucleotide sequence as set forth in SEQ ID NO:10, 11 or 12 or a sequence having at least or about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:10, 11 or 12. For example, the nucleic acid molecule encoding VP1 may comprise a nucleotide sequence as set forth in SEQ ID NO:13 or a sequence having at least or about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:13.

Also provided herein is an isolated murine parvovirus, wherein the genome comprises the nucleotide sequence set forth in SEQ ID NO:3 or a nucleotide sequence comprising at least about 70% sequence identity to SEQ ID NO:3, wherein said parvovirus is capable of infecting murine kidney cells and causing murine kidney disease.

The parvovirus genome may comprise a nucleotide sequence comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3.

It will be recognised by a person skilled in the art that viral genomic sequences and encoded polypeptides described herein may contain minor deletions, additions and/or substitutions of nucleic acid bases or amino acids, to the extent that such alterations do not negatively affect the function or structure of the virus or polypeptide.

Animal Models and Methods

Also provided herein is a murine animal for use as an animal model of kidney disease, wherein the murine animal is infected with MKPV, and to uses of such animal models. For example, the animal model may be used in the study of pathophysiological features and progression of kidney disease, optionally human kidney disease, including, for example, disease characterized by, or associated with, tubulointerstitial nephritis or kidney fibrosis. Alternatively, the animal model may be used in the screening of candidate compounds for use in the treatment of kidney disease, or in the identification of biomarkers of kidney disease.

Accordingly, in one embodiment the present disclosure provides a method for screening a candidate compound for use in the treatment of kidney disease, comprising: i) administering the candidate compound to a murine animal model infected with the parvovirus as defined in the first, second or third aspect, which animal model displays one or more symptoms of, or histopathologic features characteristic of, or associated with, the kidney disease; ii) characterizing the phenotype of the murine animal model after administration of the candidate compound; and iii) selecting the candidate compound that reverses or delays one or more symptoms, or histopathologic features characteristic of or associated with, the kidney disease, as a compound for use in the treatment of kidney disease.

Animal models according to the present disclosure will typically display one or more symptoms of, or histopathologic features characteristic of or associated with the kidney disease. The kidney disease may be a chronic kidney disease of humans, optionally immunocompromised humans. The kidney disease may comprise, or be characterized by, human tubulointerstitial nephritis or kidney fibrosis.

In animal models, symptoms and histopathologic features characteristic of, or associated with, the kidney disease may include tubular epithelial cells with enlarged nuclei (karyomegaly), the formation of eosinophilic intranuclear inclusion bodies in tubular epithelial cells, fibrosis, reduced renal mass, and kidney dysfunction (as determined, for example, by reduced proteinuria, weight loss and/or reduced urinary creatinine levels). However the scope of the present disclosure is not limited to those symptoms and features exemplified herein. There are a number of other symptoms, markers and histopathological features of kidney disease well known to those skilled in the art. Thus, in methods for screening candidate compounds for use in treating kidney disease, characterizing the phenotype of the animal model before and after administration of the candidate compound may comprise observing, determining or quantifying any one or more of these symptoms, markers and histopathological features. It is within the ordinary skill of the skilled person to determine which symptoms, markers and histopathological features may be appropriate to observe, determine or quantify in any given scenario.

The present disclosure also provides diagnostic methods to identify MKPV presence or infection. For example, provided herein is a method for detecting the presence of a parvovirus in a sample, comprising detecting one or more nucleic acids or polypeptides derived from the parvovirus, or antibodies against the parvovirus, in the sample, wherein the parvovirus comprises:
  (i) a gene encoding a non-structural (NS1) protein comprising the amino acid sequence set forth in SEQ ID NO:4, or an amino acid sequence comprising at least about 80% amino acid sequence identity thereto;
  (ii) a gene encoding a non-structural (NS2) protein comprising the amino acid sequence set forth in any one of SEQ ID NOs:5 to 7, or an amino acid sequence comprising at least about 80% amino acid sequence identity thereto;
  (iii) a gene encoding a capsid protein (VP1) comprising the amino acid sequence set forth in SEQ ID NO:8, or an amino acid sequence comprising at least about 80% amino acid sequence identity thereto; or
  (iv) the nucleotide sequence set forth in SEQ ID NO:3 or a nucleotide sequence comprising at least about 70% sequence identity thereto.

For example, known amplification or other molecular biological techniques may be used to detect the presence of MKPV in the blood or urine of an animal, in a cell line, or in an environmental sample. Such diagnostic methods may therefore be employed in screening for the MKPV in experimental animal colonies, in particular immunodeficient or immunocompromised mice. A requirement in biomedical research is that animals under study are monitored to confirm that they are free from infection with specific pathogens. There is accordingly a need for animal supply facilities and animal research facilities have stringent protocols and tests in place to monitor pathogen detection, provide animal health reports and warrant that animals shipped to and from facilities are disease and pathogen free.

Thus, in one embodiment, there is provided a method for detecting infection of an animal or cell with a parvovirus as defined herein, the method comprising contacting a biological sample derived from the animal or cell with one or more oligonucleotides specific for at least one target murine kidney parvovirus nucleic acid sequence as defined herein under conditions sufficient for amplification of the at least one target sequence producing a murine kidney parvovirus amplification product.

In another embodiment there is provided a method for detecting the presence of a parvovirus as defined herein, comprising contacting an environmental sample, or one or more nucleic acids isolated therefrom, with one or more oligonucleotides specific for at least one target murine kidney parvovirus nucleic acid sequence as defined herein under conditions sufficient for amplification of the at least one target sequence producing a murine kidney parvovirus amplification product.

A biological sample obtained from an animal for use in accordance with the present disclosure may be any suitable biological sample. The term "biological sample" is used to refer to any material, biological fluid, tissue, or cell obtained from a subject, including but not limited to blood, plasma, serum, urine or faeces. Any suitable non-biological environmental sample may be employed, such as water (for example an animal's drinking water supply), animal bedding or air dust. The air dust may be collected from airflow entering, within, or as exhaust from, an environment in which potentially susceptible animals are housed or are to be housed.

The biological or environmental sample may be obtained by any suitable method, which may be determined by a person skilled in the art. A sample may be used in its original form or may be processed to isolate nucleic acids. Furthermore, a sample may be processed such as by adding solvents, preservatives, buffers, lysis agents or other compounds or substances.

The at least one oligonucleotide may be an oligonucleotide primer for use in an amplification reaction, such as PCR. Thus, in some embodiments the terms "primer" and "oligonucleotide" may be used to refer to an oligonucleotide which acts as a point of initiation of synthesis of a primer extension product which is complementary to a nucleic acid strand (template or target sequence) under conditions suitable for primer extension and/or amplification of the target or template sequence. Conditions under which primer extension and/or target or template amplification may occur include those relating to buffer, salt, temperature and pH conditions. Primer extension and/or amplification may also require nucleotides and an agent for nucleic acid polymerization, such as DNA dependent or RNA dependent polymerase. The length of a primer and homology to the target or template sequence should be appropriate to prime the synthesis of extension products or amplicons in a specific manner. A typical primer contains at least about 10 nucleotides in length of a sequence substantially complementary or homologous to the target sequence, but somewhat longer primers may be used. Primers may typically be between 16 and 26 nucleotides in length.

Primers of the present disclosure will be capable of hybridising to a component of MKPV. In exemplary embodiments, primers of the disclosure are capable of hybridising to the NS1, the VP1 or the 3'UTR of MKPV. The primers may comprise or consist of an oligonucleotide as set forth in SEQ ID NO: 1 or SEQ ID NO:2, or primers may have at least about 90%, 91%, 92%, 93%, 94%, 95%, 96%, 97%, 98% or 99% sequence identity to the sequences as set forth in SEQ ID NO: 1 or SEQ ID NO: 2.

It will be understood that primer sequences of the present disclosure may contain minor deletions, additions and/or substitutions of nucleic acid bases such that yield or product obtained from primer extension or amplification reaction is not altered to a significant degree.

Amplification of viral DNA may be performed using polymerase chain reaction (PCR), in which a forward and a reverse oligonucleotide primer are added to a sample under conditions that allow for hybridization of the primers to a viral nucleic acid template in the sample. The primers are extended under suitable conditions and dissociated from the template in amplification cycles to increase the number of copies of the nucleic acid. Other methods of viral nucleic acid amplification include, but are not limited to, RT-PCR, quantitative real time PCR, loop mediated isothermal amplification (LAMP), DNA replication, RNA transcription, primer extension, strand displacement amplification, transcription-free isothermal amplification, repair chain reaction amplification, ligase chain reaction amplification, gap filling ligase chain reaction amplification and coupled ligase detection. Alternative methods of RNA detection may be used to detect the viral DNA, such as in situ hybridisation, southern blotting or next generation sequencing.

Primers of the disclosure may be used at about 0.1, 0.2. 0.3, 0.4, 0.5, 0.6, 0.7, 0.8, 0.9 or 1 µM, as could be determined by a person skilled in the art.

In embodiments, the amplification reaction is carried out in a mixture comprising a suitable buffer (such as a phosphate buffer or Tris buffer). The mixture may also comprise further components, such as salts (such as KCl or NaCl, $MgCl_2$ or $MgSO_4$), ammonium, one or more detergents (e.g., Triton-X100), or other additives (such as betaine or dimethylsulfoxide). The mixture may further comprise nucleotides or nucleotide analogs such as dNTPs (dATP, dCTP, dGTP, and dTTP). The reaction mixture will further comprise a polymerase, such as a DNA polymerase, such as Taq DNA polymerase.

An amplification product may be detected by any suitable method, such as a quantitative, semi-quantitative or qualitative method. For example, an amplification product may be detected using gel electrophoresis. In some embodiments, an amplification product is detected using a colorimetric assay, such as with an intercalating dye (for example, propidium iodide or SYBRO green). In other embodiments, amplification products are detected using a detectable label incorporated in one or more of the primers, for example a fluorophore. A person skilled in the art will readily be able to determine an appropriate method of detection of an amplified product.

The present disclosure also provides the use of the parvovirus as defined herein, or one or more viral polypeptides derived therefrom, for the identification of antibodies against the parvovirus in a biological or environmental sample. Thus, further provided are diagnostic methods, comprising contacting a biological sample from an animal suspected of harbouring MKPV or anti-MKPV antibodies, or an environmental sample from surrounding an animal suspected of harbouring MKPV or anti-MKPV antibodies, with the parvovirus as defined herein or one or more viral polypeptides derived therefrom, and determining whether the sample comprises antibodies specific for MKPV.

Methods for detecting or screening for the presence of antibodies that bind to one or more MKPV antigens will be well known to those skilled in the art, and include, for example, a range of serological methods and immunoassays such as ELISA assays. An exemplary VP1-derived peptide that may be employed in, for example, an immunoassay is shown in SEQ ID NO:14. The skilled addressee will appreciate that the scope of the present disclosure is not limited by reference to any specific means of identifying or detecting antibodies.

Also provided are isolated MKPV-specific antibodies, obtained, for example, from animals infected with MKPV or immunized with an isolated viral polypeptide or polynucleotide encoding one or more viral polypeptides of MKPV.

The invention also provides methods for inducing an immune response in a subject against MKPV. The method may include administering to a subject an effective amount of MKPV, optionally an attenuated or killed form of the virus or one or more components of polypeptides derived from the virus, optionally in combination with an adjuvant and/or a carrier. The MKPV, or one or more components of polypeptides derived therefrom may be administered in an amount effective to prevent or ameliorate infection of the subject by that virus or an antigenically closely related virus. Methods of inducing an immune response in accordance with the present disclosure are well known to those skilled in the art.

Vectors

The present disclosure also provides vectors comprising a nucleotide sequence described herein, such as one that encodes a VP1 capsid polypeptide or NS1 polypeptide as described herein. Typically the nucleotide sequence encoding the polypeptide may be operably linked to a promoter to allow for expression of the polypeptide. The vectors can be episomal vectors (i.e., that do not integrate into the genome of a host cell), or can be vectors that integrate into the host cell genome. Exemplary vectors include, but are not limited to, plasmids, cosmids, and viral vectors, such as AAV, lentiviral, retroviral, adenoviral, herpesviral, parvoviral and hepatitis viral vectors. The choice and design of an appropriate vector is within the ability and discretion of one of ordinary skill in the art.

As used herein, the term "viral vector" refers to a vector derived from any virus including for example MKPV as described herein or another parvovirus. Accordingly, a viral vector typically includes at least one element of origin and has the capacity to be packaged into a recombinant virus or virion. Viral vectors can have one or more of the wild-type genes of the virus from which the vector is derived deleted in whole or part, but retain functional flanking ITR sequences, which are necessary for the rescue, replication and packaging of the virion. Thus, a viral vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging. The vector and/or virion can be utilized for the purpose of transferring heterologous sequences into cells either in vitro or in vivo.

In some embodiments, the vectors of the present disclosure function to provide the MKPV capsid polypeptide and/or NS1 polypeptide, or fragments thereof, in trans for the production of viruses or virions. For example, in such embodiments, the vector may be co-transfected into a host cell with a viral vector containing a heterologous sequence flanked by ITRs and a helper plasmid or helper virus such that viruses or virions containing the capsid and/or NS1 polypeptides, and encapsidating the heterologous sequence, are produced. In other embodiments, the vectors provide the capsid and/or NS1 polypeptides, or fragments thereof, in cis for the production of viruses or virions containing the polypeptides, in which case the vector typically also contains a heterologous sequence that will be packaged into the virus or virion.

Thus, in some embodiments, the vectors of the present invention also comprise a heterologous sequence. The heterologous sequence may be operably linked to a promoter to facilitate expression of the sequence. The heterologous sequence can encode a peptide or polypeptide, such as a therapeutic peptide or polypeptide, or can encode a polynucleotide or transcript that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. As would be appreciated, the nature of the heterologous sequence is not essential to the present disclosure. In particular embodiments, the vectors comprising the heterologous sequence(s) will be used in gene therapy, for example in therapy for kidney diseases.

In particular examples, the heterologous sequence encodes a peptide or polypeptide, or polynucleotide, whose expression is of therapeutic use, such as, for example, for the treatment of a disease or disorder. For example, expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the heterologous sequence serves to alter the levels and/or activity of one or more other peptides, polypeptides or polynucleotides in the host cell. Thus, according to particular embodiments, the expression of a heterologous sequence introduced by a vector described herein into a host cell can be used to provide a therapeutic amount of a peptide, polypeptide or polynucleotide to ameliorate the symptoms of a disease or disorder. In other instances, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. Accordingly, the introduction of a heterologous sequence by a vector or recombinant virus described herein into a host cell can be used to correct mutations in genomic DNA, which in turn can ameliorate the symptoms of a disease or disorder.

Vectors suitable for use in mammalian cells are widely described and well-known in the art. Those skilled in the art would appreciate that vectors of the present invention may also contain additional sequences and elements useful for the replication of the vector in prokaryotic and/or eukaryotic cells, selection of the vector and the expression of a heterologous sequence in a variety of host cells. For example, the vectors of the present disclosure can include a prokaryotic replicon (that is, a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein.

The vectors can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly (A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors can include various posttranscriptional regulatory elements. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof. A signal peptide sequence can also be included in the vector to provide for secretion of a polypeptide from a mammalian cell. Examples of signal peptides include, but are not limited to, the endogenous signal peptide for HGH and variants thereof; the endogenous signal peptide for interferons and variants thereof; and the endogenous signal peptides for known cytokines and variants thereof. Typically, the nucleotide sequence of the signal peptide is located immediately upstream of the heterologous sequence (e.g., fused at the 5' of the coding region of the protein of interest) in the vector. In instances where the vector does not include a heterologous sequence, a signal sequence can be included in the vector downstream of the promoter so that upon insertion of a heterologous sequence, the signal peptide is in-frame with the heterologous sequence.

Also provided herein are recombinant viruses and virions comprising polypeptides described herein. For example, the recombinant virus or virion may comprise a capsid polypeptide comprising the amino acid sequence set forth in SEQ ID NO:8 or an amino acid sequence comprising at least about 80% amino acid sequence identity to SEQ ID NO:8. Alternatively or in addition the recombinant virus or virion may comprise an NS1 polypeptide comprising the amino acid sequence set forth in SEQ ID NO:4 or an amino acid sequence comprising at least about 80% amino acid sequence identity to SEQ ID NO:4. Alternatively or in addition the recombinant virus or virion may comprise an NS2 polypeptide comprising the amino acid sequence set forth in SEQ ID NO:5, 6 or 7 or an amino acid sequence comprising at least about 80% amino acid sequence identity to SEQ ID NO:5, 6 or 7. In exemplary embodiments, the recombinant virus or virion further comprises one or more heterologous sequences.

In some embodiments, methods for producing a recombinant virus or virion include introducing into a packaging cell line a nucleic acid molecule(s) encoding a capid polypeptide as described herein, an NS1 polypeptide as described herein, a suitable vector, and helper functions for generating a productive infection, and recovering a recombinant virus from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088. The helper functions may be provided by one or more helper plasmids or helper viruses comprising adenoviral helper genes.

Also provided herein are methods for introducing heterologous sequences into host cells. Typically the method may comprise contacting a host cell with a vector described herein wherein the vector comprises the heterologous sequence, or with a recombinant virus described herein wherein the recombinant virus comprises the heterologous sequence.

Also provided herein are host cells comprising MKPV, vectors or recombinant viruses as described herein. Host cells may be used to amplify, replicate, package and/or purify a polynucleotide, or express a heterologous polypeptide sequence or protein. Exemplary host cells include prokaryotic and eukaryotic cells. In some instances, the host cell is a mammalian host cell. The cell may be a cell line such as an immortalised cell line. Exemplary mammalian host cell lines include, but are not limited to, HEK-293 cells, HeLa cells, Vero cells, HUH7 cells, and HepG2 cells.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the disclosure.

EXAMPLES

The following examples are illustrative of the disclosure and should not be construed as limiting in any way the general nature of the disclosure of the description throughout this specification.

General Methods

Mice

All mice used were on the C57BL/6 background, except for Des T cell receptor (TCR) transgenic (Tg) mice, which were maintained on B10.BR. Young C57BL/6 and $Rag1^{-/-}$ mice were purchased from the Animal Resources Centre, Perth, WA, Australia, Australian BioResources, Moss Vale, NSW, Australia, or bred in-house at the Centenary Institute. All other mice, including: $Cxcr6^{gfp/gfp}$ mice; $Prkdc^{scid/scid}$ mice; Des, OT-I and P14 TCR Tg mice; Fluorescence Ubiquitin Cell Cycle Indicator (FUCCI) mice; mT/mG mice; and Ubiquitin-eGFP mice were crossed to and maintained on a $Rag1^{-/-}$ background at the Centenary Institute. Immunoglobulin transgenes were segregating in the $Prkdc^{scid/scid}$ mice. Breeding, ageing and experiments were carried out with approval of the Animal Ethics Committee, University of Sydney (2009-2013) or the Animal Ethics Committee, Royal Prince Alfred Hospital (2012-2017).

Pathology and Macroscopy

Kidney samples were assessed by a professional pathologist specializing in renal disease and by a mouse pathology service (Cerberus Sciences). Macroscopic images were taken using a Sony CyberShot through the eyepiece of a Leica M80 digital microscope ('digiscoping').

RNA Extraction

RNA extraction was performed using an RNeasy® Mini Kit (Qiagen) according to the manufacturer's instructions with slight modifications. Briefly, each kidney was snap frozen in liquid nitrogen immediately following organ harvest and then ground manually using a sterile mortar and pestle in liquid nitrogen. The sample was ground to a fine powder and extreme care was taken to ensure it did not thaw. Post-grinding, the fine suspension (tissue+liquid nitrogen) was immediately transferred to liquid nitrogen-cooled, appropriately sized, pre-weighed tubes. The ground tissue from each individual kidney was transferred into multiple tubes and weighed quickly. Lysis buffer was immediately added at this step and homogenization carried out using a 20 G needle and syringe. Lysate was passed through the syringe at least 5-10 times to obtain a homogenous lysate. Post-lysis, ethanol was added to the sample, which was then mixed and applied to the RNeasy® column. Total RNA bound to the membrane at this stage. On-column DNase digestion was carried out followed by multiple washes before the RNA was finally eluted. RNA quality was analyzed employing a Nanodrop (Thermo Fisher Scientific) and Bioanalyzer (Agilent Genomics).

Viral Metagenomics

RNA was extracted from four kidneys from 2 healthy, wild-type (C57BL/6) mice and 2 disease-affected $Cxcr6^{gfp/gfp}$ $Rag1^{-/-}$ mice. RNA libraries were prepared using Illumina's Ribo-zero Gold protocol. Stranded total RNA samples were sequenced in a 100 bp paired end run on an Illumina HiSeq 2000 platform. The primary bioinformatics analysis involved quality control (QC) checks and demultiplexing using a QC pipeline developed in-house at the at the Australian Genomics Research Facility (AGRF). The data were processed through an RNA-seq expression analysis workflow, which included alignment, transcript assembly, quantification and normalization. Differential gene expression analysis was also performed.

The per base sequence quality for all four samples was excellent, with >95% bases above Q30 across all samples. The raw sequence reads were screened for Illumina adapters, cross-species contamination and low quality bases. The low quality bases, and any possible adapter sequence, were trimmed using Trim Galore (on the world wide web at bioinformatics.babraham.ac.uk/projects/trim galore/) and Cutadapt. A minimum quality score of 20 was used, with a minimum length requirement of 50 bp.

The *Mus musculus* mm10 genome was used to create a BWA (Burrows-Wheeler Aligner) index. The index was used as a reference within the application Deconseq (Schmieder and Edwards (2011) *PLoS ONE*, 6:e17288) to remove non-viral *Mus musculus* sequences as well as bacterial, plant and fungal sequences, thereby enriching for unidentified viral sequence reads. The sequence read viral/non-viral classification was determined by applying identity threshold ranges of 70%, 80% and 90% to Percentage Identity and Coverage cut-offs. The identity threshold ranges allowed for the retaining of viral sequence reads and endogenous retroviral sequences that were initially considered as potential causative agents of disease. Each range resulted in a bin of viral/endogenous viral sequence reads that were used for the assemblies. Each bin of reads for each sample were assembled separately with the assemblers IDBA (Peng, et al (2012) *Bioinformatics* 28(11):1420-8), Trinity (Grabherr et al (2011) *Nature Biotechnology* 29, 644-652) and a Velvet/Oases (Schulz et al (2012) *Bioinformatics* 28(8): 1086-92; Zerbino and Birney (2008) *Genome Research* 18:821-829) pipeline. These assemblers were chosen due to the unknown quantity, coverage and identity of the viral reads, with each offering distinct assembly advantages. Briefly, IDBA offered an iterative approach in assembling sequences from short read data with highly variable sequencing depth; Trinity offered efficient and robust reconstruction of sequences; and the Velvet/Oases pipeline produces fragmented but accurate reconstructions of viral RNA sequences. IDBA-Tran was used with default settings to perform the assembly of the viral sequences. IDBA iteratively assembled the sequences using a kmer step of 20. MKPV was identified from the 90% to Percentage Identity IDBA-assembled sequences, which, when assembled, identified the first 4286 bp of MKPV. The final 68 bp of MKPV, representing the final 3' ITR, was subsequently identified in the Velvet/Oases build through a text search for the final 20 bp of the 4286 bp contig. The read coverage for assembled parvovirus segments was determined by aligning the trimmed raw sequences to the assembled parvovirus contigs using BWA.

Digital Gene Expression (Raw Count)

The cleaned sequence reads were aligned against the *Mus musculus* genome (Build version mm10) using Tophat Aligner (Version 2.0.14). The resulting BAM files were used in the downstream analysis. The counts of reads mapping to each known gene were summarised at gene level using the featureCounts v1.4.6-p2 utility of the subread package on the world wide web at subread.sourceforge.net/).

Reference Guided Transcript Analysis

The transcripts were assembled using Stringtie tool (v1.0.4). The alignment bam files from the Tophat alignment and the reference annotation based assembly option (RABT) were used to create known and potentially novel transcripts.

Differential Gene Expression

The differential gene expression analysis was performed using Biconductor (V3.2) and the limma package (on the world wide web at bioconductor.org/packages/release/bioc/html/limma.html). The raw gene count data from the tophat alignment stage was used as input to determine the list of differentially expressed genes.

Phylogenetic Analysis

Viruses closely related to the novel mouse parvovirus were initially identified through a Blastx analysis of the full length NS1 gene. The top five hits—accession numbers KP925531, KU563733, KX272741, JX885610, NC_032097—were all unclassified members of the family Parvovirdae of single-strand DNA viruses. A previously described reference data set of 133 virus variants representing each classified species of the Parvoviridae (Cotmore et al, *Arch Virol* 2014, 159: 1239-47) was compiled from GenBank. Sequences were trimmed and translated to contain only the NS1 gene, and then aligned using MAFFT version 7 employing the E-INS-I algorithm (Katoh and Standley, *Mol Biol and Evolution* 2013, 30: 772). After removing all ambiguously aligned regions using trimAl (Capella-Gutierrez et al, *Bioinformatics* 2009, 25:1972-3), a final NS1 sequence alignment of length 398 amino acids (n=139) was determined. A phylogenetic tree based on this alignment was then inferred using the maximum likelihood (ML) procedure implemented in PhyML 3.0 package, employing the LG amino acid substitution model with a discrete gamma distribution with four rate categories (Γ4), and SPR branch-swapping. Bootstrap support values for individual nodes were generated using 100 bootstrap replicates. To enhance clarity monophyletic groups corresponding to different parvovirus genera were collapsed.

Serum and Urine PCR Reaction

Mice suspected of carrying the virus were subjected to submandibular bleeding, and serum was obtained after coagulation. 1 µl of serum or urine was added to PCR cocktail comprising Phire II hot start Mastermix (F126L; ThermoFisher), 0.5 µM Forward Primer (5'-TACATGGC-CAAAGATCCACA; SEQ ID NO:1) and 0.5 µM Reverse Primer (5'GTGGCAGTCACCCAGCTAAT; SEQ ID NO:2). 7 µl of the completed PCR product was loaded onto 2% agarose gels prepared in 1×TAE buffer (24710-030; Invitrogen). Electrophoresis was conducted at 110 A for 60 min.

DNA Extraction and PCR Reaction from Formalin-Fixed Paraffin-Embedded Kidney Tissue DNA extraction was carried out using a QIAamp DNA Mini Kit (Qiagen) according to the manufacturer's instructions with slight modifications. 5 sections of 5 µm-thick from formalin-fixed, paraffin-embedded blocks were collected in 2 ml tubes. After xylene was added, tubes were placed on the shaker set at the lowest setting for 20-30 min. Tubes were centrifuged at full speed (18,000×g) for 10 min at room temperature, before carefully pipetting out xylene, where tissues tentatively adhered to the side of the tubes. 100% ethanol was added and placed on the shaker for 10-15 min, then centrifuged at full speed for 6 min. This was repeated once, before incubating the tubes with lids open at 56° C. to evaporate the ethanol. Tissue pellet was resuspended in tissue lysis buffer and proteinase K and subjected to 56° C. incubation for 2-3 hours with regular vortexing for efficient lysis. Second lysis buffer was added and incubated at 70° C. for 10 min. After lysis, 100% ethanol was added and the mixture was transferred to the spin column and centrifuged at full speed (18,000 g) for 1 min. Filtrate was decanted and centrifuged at full speed for an extra minute. Two wash buffers were subsequently added and centrifuged at full speed, before incubating the QIAamp membrane in the spin column with Buffer AE for a minimum of 5 min, then centrifuged at full speed for 1 min to retrieve DNA. 100 ng DNA was added to PCR cocktail comprising Phire II hot start Mastermix (F126L; ThermoFisher), 0.5 µM Forward Primer (5'-TACATGGCCAAAGATCCACA; SEQ ID NO:1) and 0.5 µM Reverse Primer (5'GTGGCAGT-CACCCAGCTAAT; SEQ ID NO:2). 50 ng of the completed PCR product was loaded onto 2% agarose (Vivantis) gels prepared in 1×TAE buffer (24710-030; Invitrogen). Electrophoresis was conducted at 110 A for 60 min.

Co-Housing

Cxcr6$^{gfp/gfp}$ Rag1$^{-/-}$ mice confirmed positive for the virus by serum and urine PCR were co-housed with Rag1$^{-/-}$ mice from Australian BioResources (Moss Vale, Australia). All mice were periodically checked to confirm and detect positivity for the virus.

Organ Fixation and Histological Analysis

Each organ was fixed in 4 ml of 10% neutral buffered formalin (Sigma-Aldrich) for 24-48 hours at room temperature, then replaced with phosphate buffered saline (PBS) to minimize over-fixation and stored at 4° C. until paraffin-embedding. Fixed organs were delivered to Veterinary Pathology Diagnostic Services, University of Sydney, for processing, paraffin-embedding, sectioning (at either 2 µm or 5 µm) and staining with hematoxylin and eosin or Milligan trichrome. Images were captured with a Leica DM6000B microscope. Some tiled images were subsequently merged using Adobe Photoshop CS6.

MicroCT

Before being subjected to MicroCT scan, each fixed kidney was placed in 20 ml of Lugol's Solution (Sigma-Aldrich) on a rocker for 48 hours at room temperature. Kidneys were then placed in a 2 ml screw-cap tube for scanning. Kidneys were scanned using an Xradia MicroXCT-400 system (Carl Zeiss XRM, USA). Images were acquired using an unfiltered source of 50 kV and 10 W. Reconstructed image stacks from each scanned kidney were visualized and analyzed using 3D image processing software Avizo (Version 9.0, FEI Visualization Sciences Group).

Sirius Red Staining

5 µm formalin-fixed paraffin-embedded kidney sections were deparaffinised with histolene and rehydrated with ethanol. The slides were then incubated in 0.1% Picro-Sirius Red (Sigma-Aldrich) at room temperature for 60 minutes. Sections were then washed twice in acidified water containing 83% glacial acetic acid (Sigma-Aldrich), dehydrated and mounted with Eukitt mounting media (Sigma-Aldrich). Stained slides were captured with a Leica DM6000B microscope.

MKPV Secondary Structure

Secondary structures of the 5' ITR of MKPV were generated using the Mfold web server for nucleic acid folding and hybridization prediction.

Tissue Processing and Flow Cytometry

Kidneys were cut into small pieces and incubated in collagenase (1 mg/ml) in 5 ml DMEM with 2% fetal calf serum (FCS) at 37° C. for 40 minutes. Samples were then filtered through an 80 µm stainless-steel mesh into a 50 ml tube (Falcon) with a further 25 ml DMEM with 2% FCS to wash cells through. Cells were then pelleted and the supernatant decanted. Cells were then resuspended in 15 ml of PBS prior to the addition of 9 ml 'isotonic' Percoll (1:9 10×PBS:Percoll) and centrifuged at 931 g for 8 minutes (brakes on). Cells were then resuspended in 20 ml of DMEM with 2% FCS and spun at 524 g for 5 minutes at 4° C. Red blood cells (RBC) were then lysed in 2 ml RBC lysis buffer (ACK buffer, prepared in-house) at 1 minute at room temperature. Cells were then washed and antibody-stained in running buffer (5% FCS, 2 mmol/L EDTA, and 0.02% sodium azide in PBS) for 1 hour at 4° C. Immediately prior to flow cytometry, cell suspensions were resuspended in running buffer containing 0.5 µg/ml DAPI (4,6-diamidino-2-phenylindole dihydrochloride; Molecular Probes, Invitrogen) for exclusion of dead cells The antibodies used in this study were: CD29 PE (clone HMβ1-1; eBioscience), CD24 PerCP-Cy5.5 (clone M1/69; eBioscience) and CD45 BUV395 (clone 30-F11; BD). To detect fibroblast activation protein (FAP), we used a FAP-selective inhibitor ARI-4613b conjugated to the infra-red fluorophore DyLight 800 (M.G., B.R., W.W.B. and J.H., manuscript in preparation). Cells were analyzed on a custom 10-laser LSR II (BD Biosciences) equipped with an infra-red laser for detection of DyLight 800. Flow cytometric data were analyzed with FlowJo software (TreeStar, Ashland, Ore).

Urinary Protein Measurements

Proteinuria was measured using the Bradford protein assay. 5 µL of undiluted urine or bovine serum albumin (BSA) standards was added to each well of a 96-well flat bottom plate (Falcon), followed by mixing with 250 µL Bradford Reagent (BioRad) and a 5 minute incubation at room temperature. Absorbance levels were measured at 595 nm using a POLARstar Omega Spectrophotometer (BMG LABTECH). Protein concentrations were extrapolated from the BSA standard curve.

Urine Creatinine Measurements

Urinary creatinine was measured using a commercial kit (Crystal Chem). 8 µl urine (neat or at a 1:2 dilution in 0.9% saline) or the calibrator was added to each well of a 24-well flat bottom plate (Falcon), followed by 270 µl of Reagent CC1 and incubated at 37° C. for 5 minutes. Sample absorbance at 550 nm was then measured using a POLARstar Omega Spectrophotometer (BMG LABTECH). This was then followed by adding 90 µl of Reagent CC2, a further 5 minute incubation at 37° C., and a second absorbance reading at 550 nm. The change in absorbance values was then compared to the calibrator, and the mouse creatinine concentration subsequently calculated.

Serum Creatinine Measurements

Serum creatinine was measured using a colorimetric assay kit (Cayman Chemical) based on the Jaffe reaction. Blood was collected from submandibular bleeding of mice and left for clotting for a minimum 1 hour at room temperature. Serum was retrieved after centrifuging samples at 4000 g for 5 minutes at room temperature. 30 µl of serum (or standard) was added to each well of a 96-well flat bottom plate (Falcon), followed by 50 µl creatinine reaction buffer and 50 µl colour reagent as per the manufacturer's instructions. Sample absorbance at 490 nm was measured at 1 minute and 7 minutes using a POLARstar Omega Spectrophotometer. Serum creatinine concentration was then calculated from the change in absorbance of each sample and the standard curve.

Epidermal Growth Factor (EGF) ELISA

Urinary EGF concentrations were measured using the Mouse EGF DuoSet® ELISA kit (R&D Systems) and conducted as per the manufacturer's instructions. Subsequent to overnight coating of a 96-well plate (Corning Costar) with the capture antibody at 200 ng/ml, the plate was washed twice with 0.05% Tween® 20 (Sigma-Aldrich) in PBS. The plate was then blocked with 1% BSA (Sigma-Aldrich) in PBS for 1 hour and washed twice. A 100 µl sample (or standard) was added for a 2 hour incubation at room temperature, followed by 2 washes. The following urine dilutions were achieved with the diluent (1% BSA in PBS), as determined by the age group and the mouse strain. For all wild-type (C57BL/6) samples and mice of the disease affected $Cxcr6^{gfp/gfp}$ $Rag1^{-/-}$ at 1-130 days old, 1:12800, 1:25600, 1:51200 were used. For the diseased 131-190 days old mice, 1:6400, 1:12800, 1:25600 were used. Lastly, any diseased mouse greater than 191 days old had 1:800, 1:1600, 1:3200 dilutions. Detection antibody with the final concentration of 200 ng/ml was then added for another 2 hours at room temperature and washed twice. Streptavidin-HRP (provided in the kit) at 1:200 dilution in the diluent was further incubated for 20 minutes at room temperature in the dark, and twice washed. 1-Step™ Ultra TMB-ELISA Substrate Solution (Thermo Scientific) was incubated at room temperature for 20 minutes, followed by adding 2N sulfuric acid to stop the reaction. Absorbance was measured by a POLARstar Omega Spectrophotometer (BMG LABTECH) at 450 nm and 570 nm to account for optical correction of the plate. Following the optical correction, absorbance of each sample and the standard curve were used to calculate the concentration of urinary EGF.

Latent TGFβ Binding Protein 2 (LTBP2) ELISA

Urinary LTBP2 levels were measured using the Mouse LTBP2 Sandwich ELISA Kit (LifeSpan Biosciences, Inc.). 100 µl of mouse urine samples at neat or 1:2 dilution (with diluent provided) or standard were added to the capture antibody pre-coated plate for 2 hours at 37° C., followed by aspirating the liquid. Detection Reagent A at 1:100 was added for another 1 hour incubation at 37° C. After aspiration, the wells were washed thrice with the wash buffer provided. Detection Reagent B at 1:100 was then added for a 1 hour incubation at 37° C., followed by aspirating and washing 5 times. TMB substrate from the stock solution was directly added to each well and incubated for 30 minutes at 37° C., followed by stop solution. The absorbance levels were then measured using a POLARstar Omega Spectrophotometer (BMG LABTECH) at the wavelength of 450 nm. Concentrations of LTBP2 were calculated from the absorbance values and the standard curve.

MKPV Serostatus ELISA

An oligopeptide-based direct ELISA was designed to assess the serostatus of mice to MKPV. The oligopeptide THVATTTQGCFRISLHLA (SEQ ID NO:14) was initially selected based on its potential immunogenicity, then synthesised and resuspended in DMSO (Sigma) at a 10 mg/mL stock. The oligopeptide was diluted in bicarbonate coating buffer (100 mM $Na_2CO_3$ and 100 mM $NaHCO_3$ in MilliQ water, pH 9.1) at a working concentration of 2.5 ug/ml, of which 100 µl was aliquoted to each coated well of the 96 well U-bottom non-treated vinyl plate (Costar, Corning) for overnight incubation at 4° C. Each well was aspirated and washed 6 times with 1×PBST (1×PBS with 0.05% Tween-20, Sigma) the next day. 200 µl of 1% Bovine Serum Albumin (BSA, dissolved in 1×PBS, Sigma, 0.22 µm filtered) was then added for blocking and incubated at room temperature for a minimum of 1 hr, followed by aspiration and washing 6 times with 1×PBST. 100 µl of the serum sample at a dilution of 1:100 in 1% BSA was added to each well. It was incubated for 1 hr at room temperature before being aspirated and washed 6 times with 1×PBST. Subsequently, 100 µl of secondary antibody goat anti-mouse IgG (H+L) conjugated with horseradish-peroxidase (Invitrogen, ThermoFisher) at 1:10000 dilution in 1% BSA was added to each well for a further 1 hr incubation at room temperature in the dark. Each well was aspirated and washed 6 times with 1×PBST. 100 µl of 1-Step Ultra TMB-ELISA Substrate Solution (ThermoFisher) was added and incubated at room temperature in the dark for 5-10 minutes for the colour to develop, followed by adding 50 µl of 2N sulfuric acid (Sigma) to stop the reaction. Absorbances were subsequently measured using the POLARstar Omega Spectrophotometer (BMG LABTECH) at two wavelengths, 450 nm and 570 nm for optical correction of the plate, before being compared with other samples to assess the serostatus across different mice to MKPV.

AAV Packaging

A plasmid expressing a human-optimised MKPV cap gene was transiently co-transfected, using a standard calcium-phosphate precipitation technique, into HEK293D cells, along with plasmid encoding an AAV2 vector (pAAV2-LSP5.SV40int.egfp, consisting 5' to 3' of an AAV2 ITR, a liver-specific promoter (LSP), an SV40 intron, eGFP coding sequence, and a second AAV2 ITR), and a pXX6 helper plasmid expressing one of six different AAV2 NS1 proteins (from serotypes R1-R6). Viral genome copies were determined by quantitative PCR of culture supernatants for packaged GFP and AAV ITRs.

Statistical Analysis

Statistical analyses were performed by using Prism 7 software (GraphPad Software, La Jolla, Calif.). P values of differences between groups were determined by using a 2-tailed unpaired Mann-Whitney U test. A statistical difference was assumed if the P value was less than 0.05.

Example 1—Identification and Characterization of a Novel Virus, Mouse Kidney Parvovirus (MKPV)

The inventors observed that middle-aged mice within a number of disparate immunodeficient colonies at their facility unexpectedly died, the likely cause of death being renal failure. The kidneys of moribund mice appeared shrunken, pale and pitted upon necropsy, and highly fibrotic by histology (data not shown). All other tissues from diseased mice appeared morphologically and histologically normal (data not shown). Retrospective analysis of the necropsy records revealed a high penetrance of kidney disease throughout many generations of $Rag1^{-/-}$ and $Prkdc^{scid/scid}$ mice, both of which lack T and B cells, with the age of death usually occurring between 200 and 300 days (FIG. 1), much shorter than the natural lifespan of mice (>500 days).

Histopathological assessment of affected kidneys identified tubular epithelial cells with enlarged nuclei (karyomegaly) and chromatin clearing associated with the formation of large, glassy, eosinophilic intranuclear inclusion bodies (FIG. 2). Nuclear inclusion or 'Cowdry' bodies are a classic hallmark of viral infection, and their presence in renal tubular epithelial cells is observed in polyomavirus-associated nephropathy. A viral etiology for the mouse kidney disease was therefore suspected. However, since all murine colonies at the facility and its vendors are free of known specified infectious agents, including mouse polyomavirus, it was likely that any causative agent would be hitherto uncharacterized such that a candidate-based approach to its identification was unfeasible.

Using a metagenomics approach, RNA was extracted from diseased kidneys and unaffected wild-type controls, the ribosomal RNA removed, and the remaining material sequenced. RNA sequencing was chosen over DNA sequencing to accommodate the possibility that the kidney disease was driven by an RNA virus. RNA sequences were pre-screened in silico for extraneous sequences deriving from plants, bacteria and fungi as well as mouse (*Mus musculus*) prior to assembly. This protocol left ~55,000 unassigned sequences from each mouse, many of which represented unannotated mouse genes, endogenous retroviruses and low-abundance DNA contaminants (data not shown).

Examination of the longest and most abundant sequences isolated from the more moribund mouse identified coding sequences with homology to parvoviral non-structural (NS1 and NS2) and structural (capsid; VP1) proteins. No other genes resembling replication-competent viruses were found. The inventors then used these sequences to perform a BLAST nucleotide search of the unassigned sequences from the second (less severely affected) mouse, which identified four homologous sequences. Manual alignment of the six sequences revealed a complete 4354 bp viral genome, the fidelity of which was confirmed by PCR and Sanger sequencing of DNA isolated from kidneys of disease-affected mice (SEQ ID NO:3). With the complete DNA sequence, the inventors were then able to measure RNA coverage across the viral genome within each sample (FIG. 3). This revealed full expression of NS1 and VP1 mRNA in both animals, consistent with productive infection within the kidneys of these mice. The inventors therefore termed this new virus mouse kidney parvovirus (MKPV).

Example 2—Detection and Transmissibility of MKPV

PCR primers specific for the MKPV NS1 gene (SEQ ID NO: 1 and SEQ ID NO: 2) were designed and used to test the serum and urine of a number of immunodeficient mouse lines for the presence of viral DNA. Viral amplicons were detected in mouse colonies in which kidney disease had been observed but was absent from disease-free lines (FIG. 4). Viral DNA was also detected within the faeces of affected mice (data not shown), although no pathological changes within the gastrointestinal tract were observed. PCR amplification also detected MKPV NS1 DNA from the kidneys and urine of disease-affected NOD.Cg-$Prkdc^{scid}$ $Il2rg^{tm1Wjl}$/

SzJ (NSG) mice from the Memorial Sloan Kettering Cancer Center, but not from unaffected mice from MSKCC (data not shown).

To test for horizontal transmissibility of the virus, MKPV PCR Cxcr6$^{gfp/gfp}$ Rag1$^{-/-}$ mice were co-housed with virus-free Rag1$^{-/-}$ mice obtained from a vendor with no history of kidney disease in their animals. After 50-80 days, viral DNA was detectable within the serum and urine of the co-housed animals (FIG. 5A), which subsequently developed and succumbed to kidney disease a further 200 days later (FIG. 5B). When virus-bearing mice were co-housed with immune-competent wild-type mice, viral DNA was detected within the faeces but never in the serum, kidney or urine (data not shown). Collectively, these data suggest that MKPV is transmitted via an oral-fecal route and that its dissemination to and/or persistence within the kidney is controlled by the adaptive immune system.

Example 3—Origin of MKPV

Figure 3:
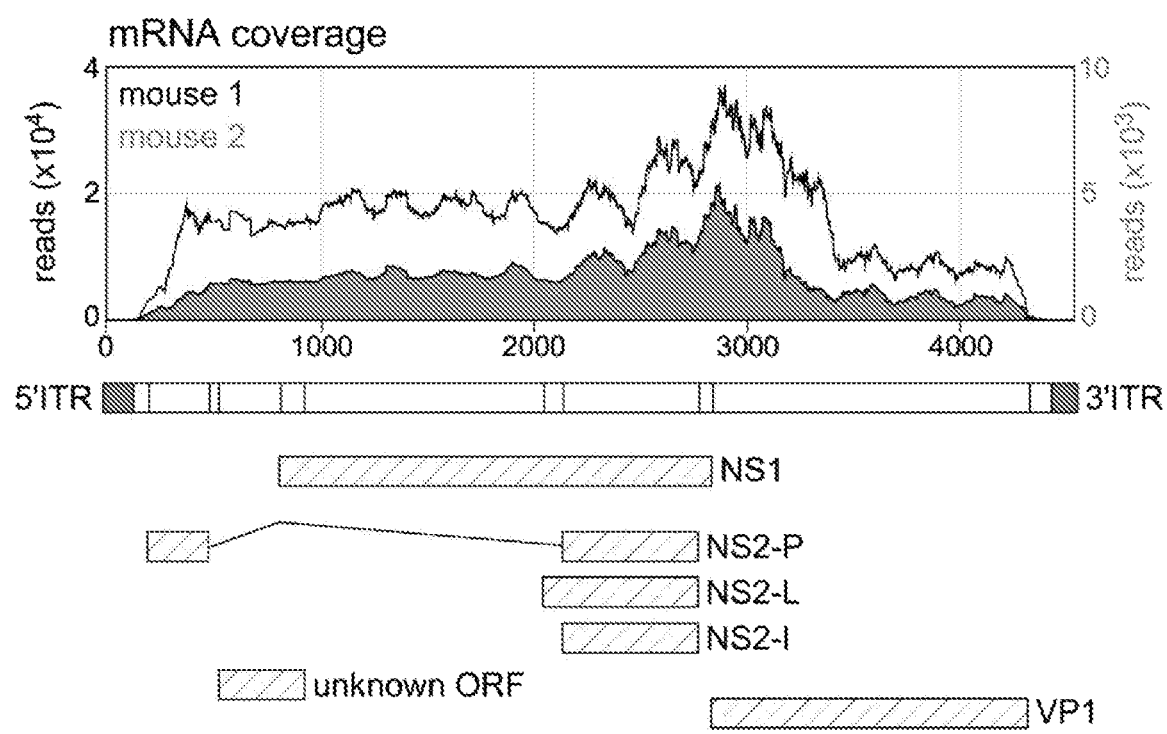
FIG. 3. Identification of mouse kidney parvovirus (MKPV). Top: mRNA reads mapped to the final assembled viral genome for two inclusion body nephropathy-affected mice (black line and blue histogram). Middle: Schematic of the mouse kidney parvovirus sequence. Filled boxes indicate location of inverted tandem repeats (ITRs). Bottom: Putative transcripts encoding NS1 (non-structural protein 1), NS2 (non-structural protein 2), VP1 (viral protein 1) and an open reading frame (ORF) of unknown significance. Depending upon splicing and start codon, NS2 could comprise three variants, named NS2-P, NS2-L and NS2-I based on the second amino acid predicted polypeptide sequence.
Figure 4:
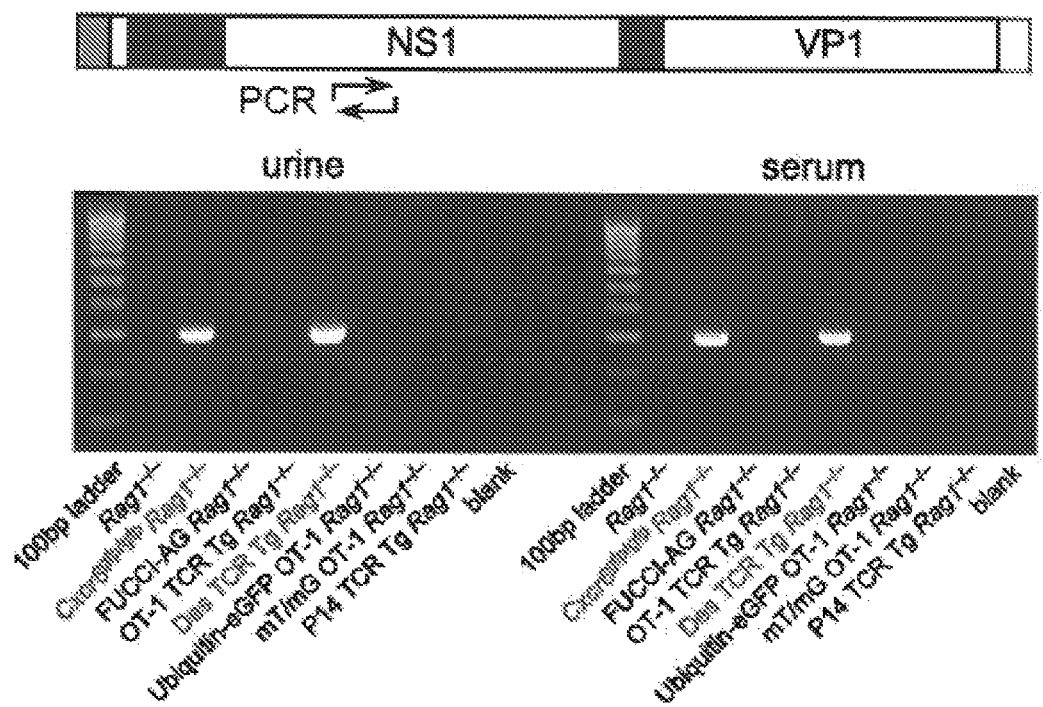
FIG. 4. PCR amplification of viral NS1 DNA from urine and serum of disease-affected lines (Cxcr6$^{gfp/gfp}$ Rag1$^{-/-}$ and Des T cell receptor (TCR) transgenic (Tg) Rag1$^{-/-}$ mice) but not unaffected mice.

The sequencing enabled the assembly of a complete 4354 bp parvovirus sequence (SEQ ID NO:3), including the 5' inverted tandem repeats (ITRs) that form the classic 'bubble' stem-loop structures typical of many parvoviruses. Parvoviral ITRs are not normally transcribed, as reflected in the RNA coverage data (FIG. 3), so the identification of the 5' and 3' ITRs may have been due to the presence of low level viral DNA contamination.

Figure 6:
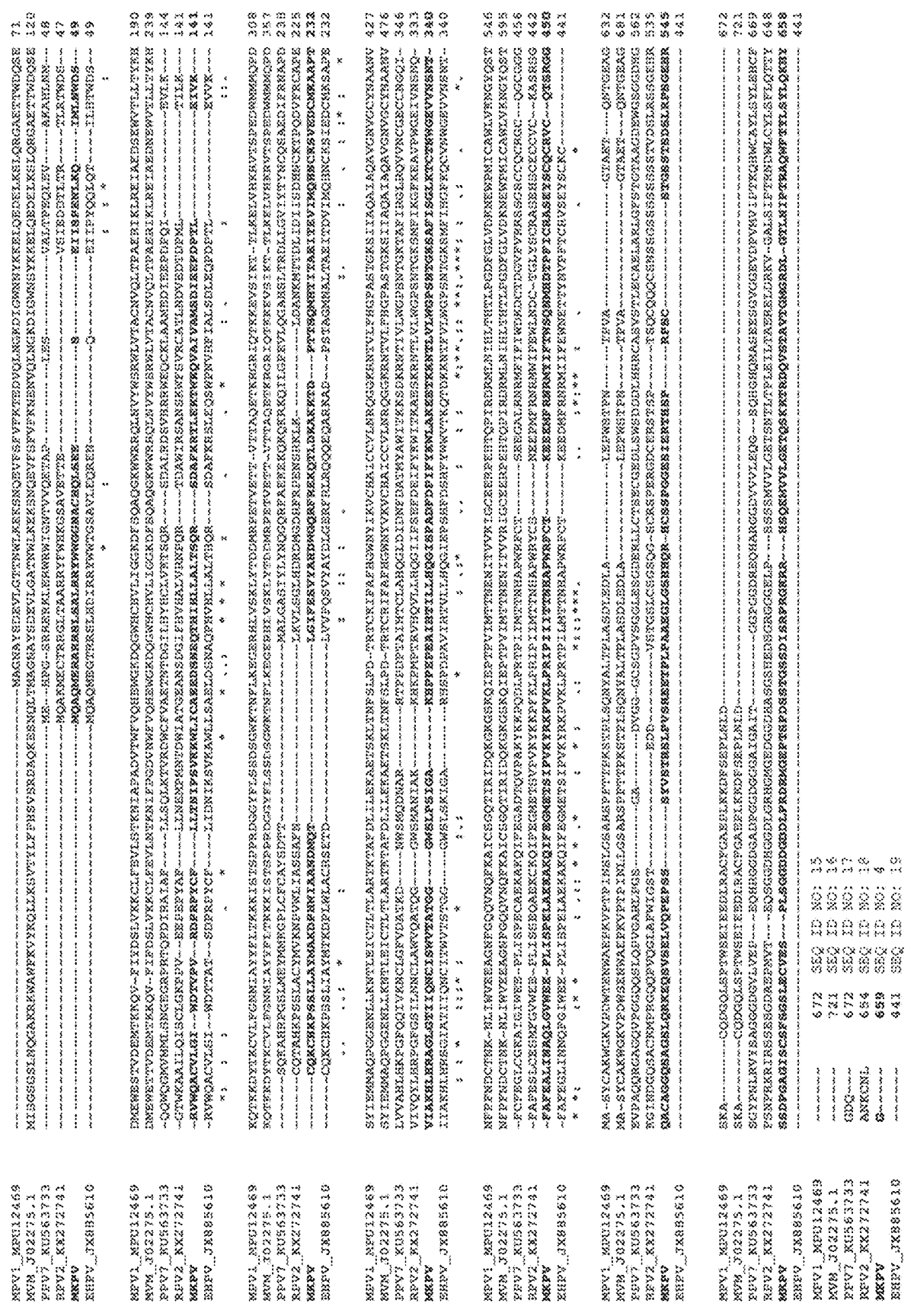
Figure 7:
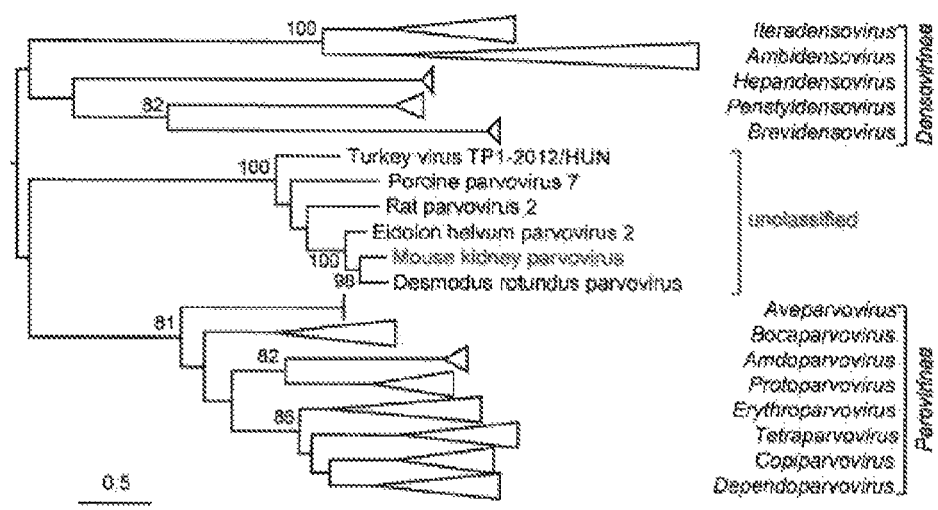
FIG. 7. Phylogenetic analysis of the Parvoviridae family based on conserved areas of the NS1 protein. Bootstrap support values >70% are shown for key nodes. Branch lengths are scaled according to the number of amino acid substitutions per site, and the tree is rooted to show the distinction between the Parvovirinae and the Desnovirinae.

Parvoviruses are small, highly diverse single-strand DNA viruses capable of infecting many animal species, including both vertebrates (Parvoviridae) and invertebrates (Desnovirinae). A number of mouse parvoviruses have been identified, all of which exhibit high sequence similarity and belong to the same genus (Protoparvovirus) (Joh et al. (2013) *Exp Mol Pathol* 95, 32-37). Mouse parvovirus infections are clinically silent in immune-competent animals but can occasionally cause bone marrow anomalies in immunodeficient strains. Amino acid sequence analysis of MKPV suggested that it was highly divergent from the known mouse parvoviruses. To gain further insight into the evolutionary relationship of MKPV and other members of the family Parvoviridae, a phylogenetic analysis was performed using conserved regions of the NS protein. Strikingly, MKPV exhibited a close evolutionary relationship with two viruses isolated from the faeces of pigs and wild rats, and was most closely related to parvoviruses isolated from Old World fruit bats (*Eidolon helvum*) and common vampire bats (*Desmodus rotundus*) in Ghana and Brazil, respectively (FIG. 6). Hence, MKPV is clearly a member of a divergent and currently unclassified genus of parvovirus (FIG. 7). The capsid protein sequences were too divergent for equivalent evolutionary analysis of the VP gene.

Example 4—Pathology and Disease Progression of MKPV-Infected Mice

Given the potential utility of studying MKPV infection for understanding chronic kidney disease, the inventors conducted a more detailed investigation of the pathology and disease progression in MKPV-infected mice. Moribund mice demonstrated extensive microscopic and macroscopic fibrotic changes (FIGS. 8A and 8B) as well as significantly reduced renal mass after 200 days of age (FIG. 8C). Fibrosis appeared to expand from perivascular locations, consistent with a pericyte origin, but this was accompanied by surprisingly little inflammatory infiltrate (data not shown).

The inventors detected MKPV in inclusion body nephropathy-affected mice (data not shown), strongly suggesting that inclusion bodies are formed as a result of MKPV propagation within the tubular epithelial cell nuclei. Quantitative PCR was used to demonstrate an increase in renal viral load with increasing age in affected mice (data not shown). This supports the contention that MKPV propagation within the kidney is the ultimate cause of death in these animals. The qPCR data indicate that 100 million-fold expansion of MKPV in the kidney as the mouse ages results in the direct and indirect destruction of the kidney parenchyma (through viral infection and secondary inflammation and fibrosis, respectively) until such time as kidney failure occurs.

Figure 9:
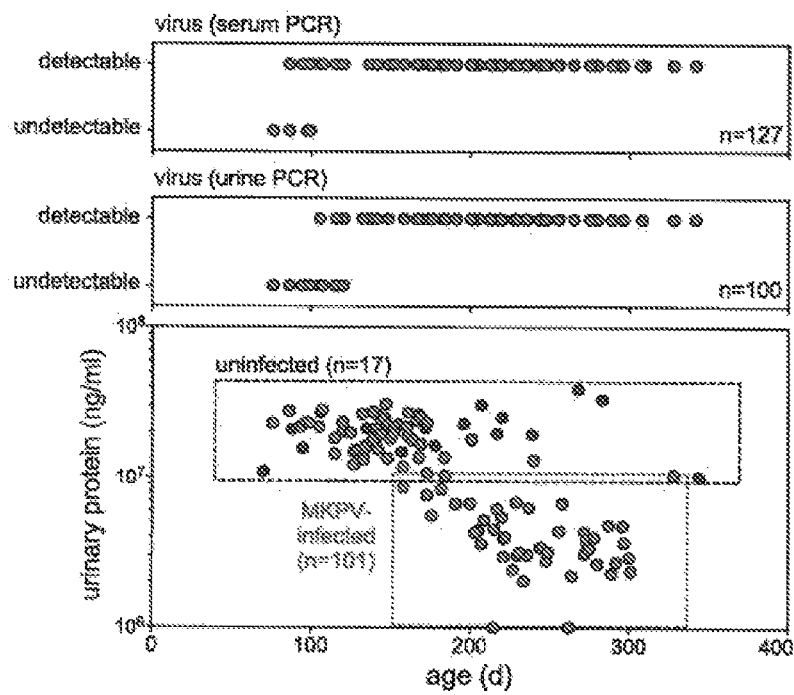
FIG. 9. Chronology of viremia and urinary protein in Cxcr6$^{gfp/gfp}$ Rag1$^{-/-}$ mice with age (red circles). For the proteinuria measurements, wild-type and uninfected Rag1$^{-/-}$ mice have been included for comparison (black circles).
Figure 10:
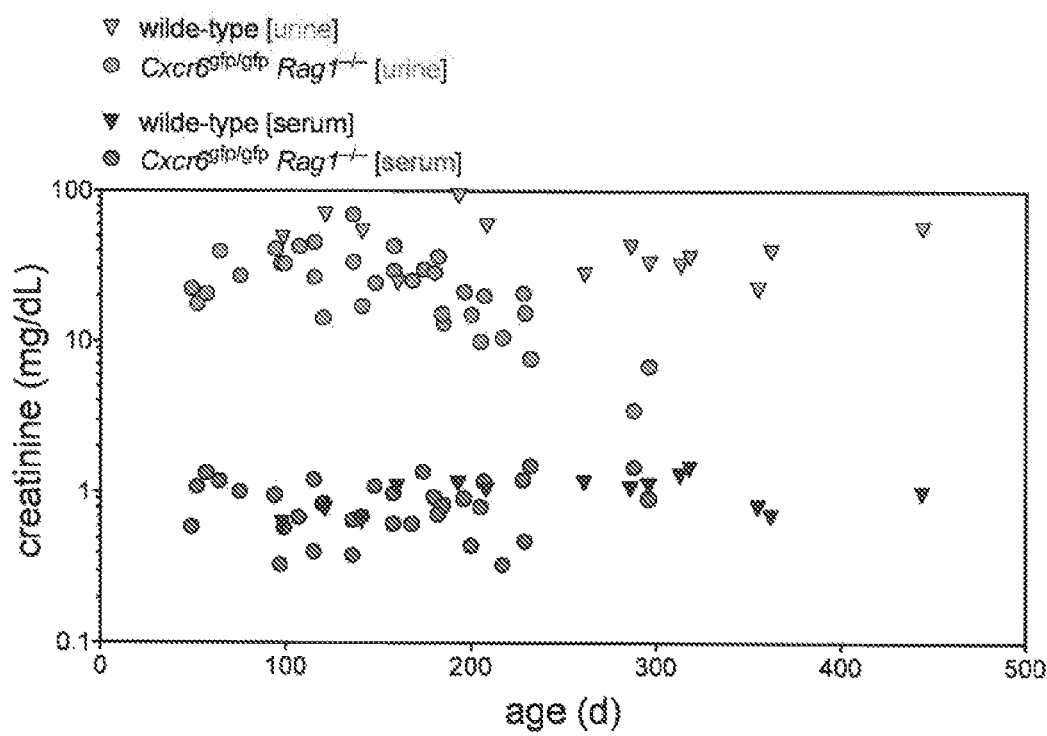
FIG. 10. Urinary and serum creatinine levels in MKPV-infected mice. Creatinine levels in the urine (orange circles) and serum (red circles) of MKPV-infected Cxcr6$^{gfp/gfp}$ Rag1$^{-/-}$ mice with age. Urinary and serum creatinine in wild-type and uninfected Rag1$^{-/-}$ mice have been included for comparison (grey and black upside-down triangles, respectively).

Viremia and disease progression were also tracked in a cohort of Cxcr6$^{gfp/gfp}$ Rag1$^{-/-}$ mice, one of the disease-affected lines. Mice became universally PCR for virus in the serum and urine after approximately 100 days of life (FIG. 9), suggesting that MKPV is highly infectious with 100% penetrance. Between 150 and 250 days of age, the normally elevated rodent proteinuria dropped dramatically (FIG. 9), which coincided with weight loss in MKPV-infected animals (data not shown), likely reflecting severe kidney dysfunction by this time. Serum creatinine remained consistently low throughout the life of these mice (FIG. 10), possibly due to the countering effects of weight loss and renal dysfunction on creatinine production and clearance, respectively. Consistent with this, urinary creatinine levels dropped from 150 days in MKPV-infected mice (FIG. 10). Collectively, these data demonstrate that MKPV-infected mice experienced kidney dysfunction for 4-5 months, fulfilling the pathological criteria of chronic kidney disease.

The mechanisms underlying tissue fibrosis are still relatively poorly understood. Fibrosis is defined as the excessive deposition of extracellular matrix, particularly collagen, within tissues, which results in functional impairment of organs. The source of collagen is usually associated with mesenchymal cells, namely fibroblasts and myofibroblasts. Wnt signalling and certain cytokines, primarily TGFβ, are believed to be the drivers of collagen production by these cells. The inventors therefore sought to identify the molecular mechanisms underlying the fibrotic disease in MKPV-infected mice, and assess the comparability of MKPV-driven chronic kidney disease to human chronic kidney disease. This was facilitated by the RNA sequencing approach taken to identify MKPV, which also enabled an assessment of the host response to MKPV-infection. Attesting to the validity of the transcriptomics data, the two most highly upregulated genes in disease-affected kidneys were Havcr1 (encoding kidney injury molecule-1) and Lcn2 (encoding lipocalin 2), both well-established kidney injury biomarkers. Despite the lack of inflammatory infiltrate by histology, a number of immune system genes were upregulated in diseased kidneys, particularly those encoding complement. Complement genes can be expressed by kidney proximal tubular epithelial cells, and their expression is regulated by TGFβ. Transcription of fibrinogen complex proteins was also increased in MKPV-infected kidneys, noteworthy because fibrinogen has been flagged as a potential therapeutic target in fibrotic kidney disease (Schack et al. (2016) *Stem Cells Int* 2016, 1319578).

Consistent with the histological data, increased expression was observed for genes coding for TGFβ and collagen (Tgfb1, Col1a1, Col3a1) and regulators of this pathway (Fosl2, Wnt4, Serpine1), as well as markers classically expressed by myofibroblasts (Acta2 and Vim). This was further supported by the presence of kidney-resident fibroblasts expressing CD24 (FIG. 11), a recently-identified marker of myofibroblast conversion. Taken together, these data demonstrate that MKPV infection drives a progressive, highly penetrant fibrotic phenotype associated with myofibroblast activation, TGFβ signalling and collagen production.

Example 5—Biomarkers of Kidney Fibrosis

It has been well-established through animal experimentation and clinical experience that the severity of tubulo-interstitial fibrosis is a major determinant of renal dysfunction. However, assessing fibrosis in a clinical setting is a significant challenge, and sensitive urine biomarkers are still required. By filtering the RNA-seq data for secreted gene products, the inventors identified a number of putative biomarkers for fibrotic changes within the kidney. The inventors then focused on two proteins, epidermal growth factor (EGF; decreased) and latent TGFβ-binding protein 2 (LTBP2; increased), since these molecules have recently been identified as putative biomarkers of kidney fibrosis in humans (Haase et al. (2014) *Biomark Med* 8, 1207-1217; Ju et al. (2015) *Sci Transl Med* 7, 316ra193). Consistent with the transcriptomics data, urinary EGF was significantly decreased in MKPV-infected mice (FIG. 12A), while LTBP2 was detectable in one third of MKPV-affected mice and undetectable in normal mice, with the exception of one aged animal (FIG. 12B). Collectively, these data indicate that MKPV infection within the kidney drives a chronic tubulointerstitial nephritis that functionally and biochemically resembles human chronic kidney disease.

The known, closely-related murine parvoviruses, including MPV-1 and Minute Virus of Mice, demonstrate tropism for hematopoietic cells and generally do not cause clinical signs, even in immunocompromised mice. In contrast, MKPV, which only shows a distant evolutionary relationship with those viruses, displays remarkable tropism for renal tubular epithelial cells and induces overt pathology resulting in fibrosis and chronic kidney disease. This kidney-tropism may prove useful for targeting of tubular epithelial cells in vivo using the MKPV capsid, particularly with adeno-associated viral vectors, which are also parvoviruses.

The histopathological features of MKPV infection have been described in wild-type mice in at least one other facility (Baze et al (2006) *Comp Med* 56, 435-438). It will therefore be important to determine the distribution of MKPV in animal colonies inside other institutions in Australia and around the world. The long-term persistence of MKPV within several immunodeficient lines at the Centenary Institute facility suggests that, once established, this virus is not readily removed from animal facilities.

Example 6—MKPV Detection

Figure 13:
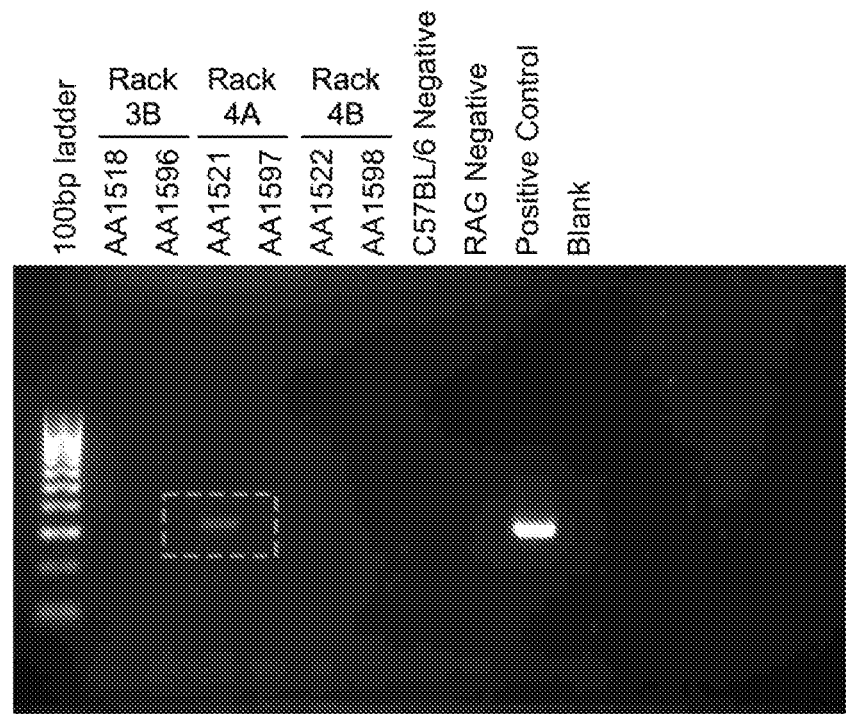
FIG. 13. PCR detection of MKPV in the urine of an outbred Swiss mouse. Detection of viral DNA by PCR in the urine (dashed box) of an outbred sentinel Swiss mouse. This mouse was a sentinel for a rack that housed MKPV-infected Cxcr6$^{gfp/gfp}$ Rag1$^{-/-}$ mice. MKPV transmission to the Swiss mouse is presumed to have occurred as a result of bedding transfer.

MKPV viral DNA was detected by PCR in the urine of an outbred sentinel Swiss mouse (FIG. 13). This mouse was a sentinel for a rack that housed MKPV-infected Cxcr6$^{gfp/gfp}$ Rag1$^{-/-}$ mice. MKPV transmission to the Swiss mouse is presumed to have occurred as a result of bedding transfer. This data indicates that MKPV can productively infect the kidneys of immune-sufficient (wild-type) mice, and that sentinel protocols can be developed to detect MKPV, for example by urine analysis, serological test or testing of bedding.

Figure 14:
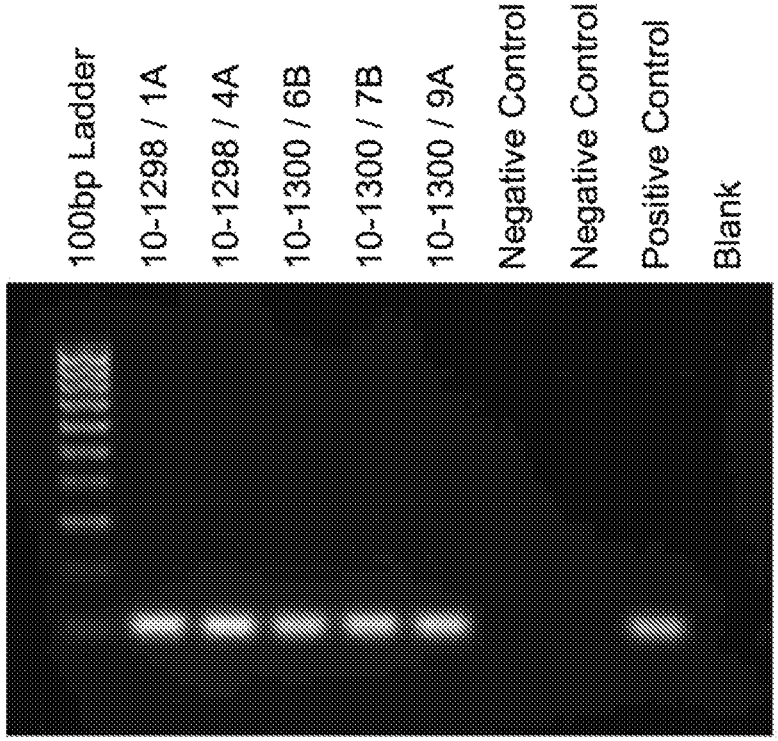
FIG. 14. Detection of MKPV in mice with histopathologically-confirmed inclusion body nephropathy at Cerberus Sciences Laboratory. Detection of viral DNA by PCR in formalin-fixed paraffin-embedded kidney tissues from 5 sentinel Prkdc$^{scid}$ mice that were housed in an independent (non-Centenary Institute) Australian animal facility and had histologically-confirmed inclusion body nephropathy.

MKPV DNA was also detected by PCR in kidney tissues from 5 sentinel Prkdc$^{scid}$ mice that were housed in an independent Australian animal facility and had histologically-confirmed inclusion body nephropathy (FIG. 14). This result further strengthens the association of MKPV with inclusion body nephropathy and indicates that MKPV is likely prevalent in multiple Australian-based animal facilities. It also demonstrates that PCR can be used to detect MKPV in formalin-fixed paraffin-embedded kidney tissues of inclusion body nephropathy-affected mice.

Figure 15:
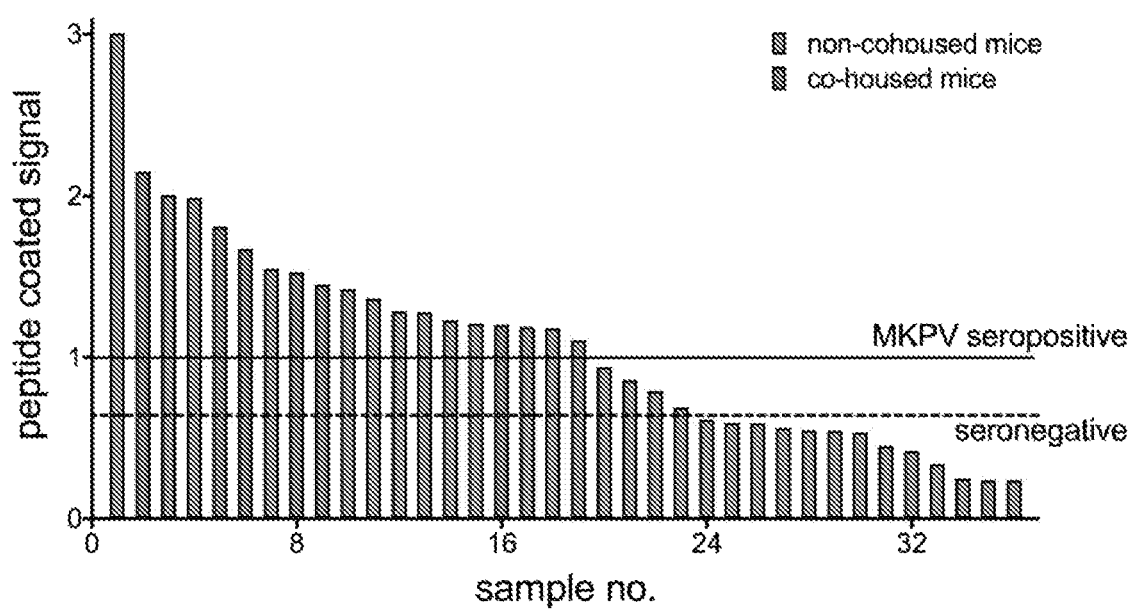
FIG. 15. Serological test for MKPV. ELISA for MKPV VP1 peptide THVATTTQGCFRISLHLA (SEQ ID NO:14). The graph depicts the signal intensity (arbitrary units) from an ELISA of serum collected from 36 individual immunocompetent mice. Samples are ordered in order of signal intensity. Samples nos. 2, 5, 6, 8, 9 and 16 represent C57BL/6 mice that were co-housed with MKPV-infected Cxcr6$^{gfp/gfp}$ Rag1$^{-/-}$ mice and serve as an indicator of seropositive mice. Grey bars indicate non-co-housed mice of varying immunoreactivity to the MKPV peptide. Seronegative animals are indicated by the dashed line.

Demonstrating the ability of a serological test to detect MKPV, an ELISA was conducted using the VP1-derived peptide THVATTTQGCFRISLHLA (SEQ ID NO:14) to detect MKPV seropositive immune-competent mice. The results are shown in FIG. 15.

Protein from MKPV-infected kidneys of a Cxcr6$^{gfp/gfp}$ Rag1$^{-/-}$ mouse was analysed by mass spectrometry. Numerous peptides derived from MKPV NS1 and VP1 proteins were detected as shown in FIG. 16. These data suggest the identity of those NS1- and VP1-derived peptides that are more likely to be detected by mass spectrometry. The detected peptides may also represent appropriate initial target sequences for use in an ELISA or other serological test.

Example 7—Vector Packaging

Figure 17:
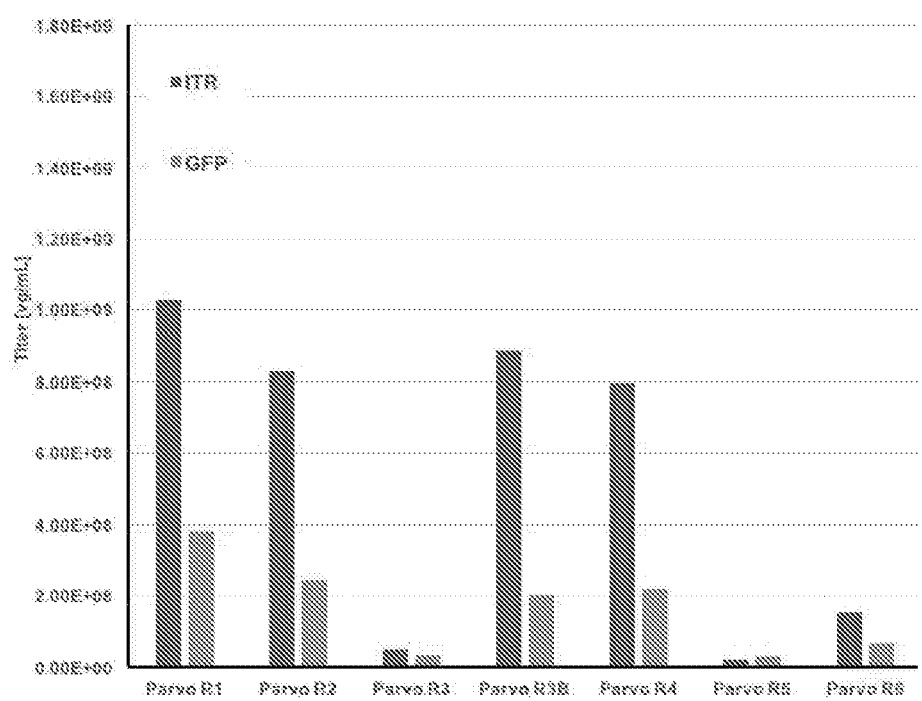
FIG. 17. MKPV VP1 packages AAV. Titres (vector genomes (vg) measured by qPCR for AAV2 ITR (left hand bar) or for GFP (right hand bar)) of recombinant viruses encoding GFP packaged by transiently transfecting the MKPV cap gene (encoding MKPV VP1), a GFP-encoding recombinant AAV2 vector, plus one of six different AAV rep genes (encoding NS1 from AAV serotypes R1-R6) into HEK293 cells. All bars represent AAV virions that were packaged entirely using MKPV VP1.

The ability of the MKPV VP1 capsid to be packaged into an AAV vector was investigated. Briefly, a plasmid expressing a human-optimised MKPV cap gene was transiently co-transfected into HEK293D cells, along with plasmid encoding an AAV2 vector and GFP. Titres of recombinant viruses encoding GFP packaged by transiently transfecting the MKPV cap gene, the GFP-encoding recombinant AAV2 vector, plus one of six different AAV rep genes are shown in FIG. 17. The data demonstrate that MKPV VP1 is compatible with standard AAV packaging, making it amenable for gene targeting pipelines.

The invention claimed is:

1. A method for detecting the presence of a parvovirus in a sample, comprising detecting one or more nucleic acids or polypeptides derived from the parvovirus, or antibodies against the parvovirus, in the sample, wherein the parvovirus comprises:
   (i) a gene encoding a non-structural (NS1) protein comprising the amino acid sequence set forth in SEQ ID NO: 4, or an amino acid sequence comprising at least about 80% amino acid sequence identity thereto;
   (ii) a gene encoding a non-structural (NS2) protein comprising the amino acid sequence set forth in any one of SEQ ID NOs: 5 to 7, or an amino acid sequence comprising at least about 80% amino acid sequence identity thereto;
   (iii) a gene encoding a capsid protein (VP1) comprising the amino acid sequence set forth in SEQ ID NO: 8, or an amino acid sequence comprising at least about 80% amino acid sequence identity thereto; or
   (iv) the nucleotide sequence set forth in SEQ ID NO: 3 or a nucleotide sequence comprising at least about 70% sequence identity thereto.

2. A method according to claim 1, comprising detecting one or more nucleic acids derived from the parvovirus in the sample.

3. A method according to claim 2, comprising contacting the sample, or one or more nucleic acid sequences isolated from the sample, with one or more oligonucleotides specific for at least one target nucleic acid sequence of the parvovirus defined in claim 1, under conditions sufficient for amplification of the at least one target sequence.

4. A method according to claim 1, wherein the method comprises the use of one or more polypeptides derived from the parvovirus for the detection of antibodies against the parvovirus.

5. A method according to claim 1, wherein the sample is a biological sample or an environmental sample.

6. A method according to claim 1, wherein the sample is derived from a murine laboratory animal or the environment of said animal.

7. A method according to claim 1, wherein the sample is derived from an immunocompromised or immunodeficient mouse, or the environment of said mouse.

* * * * *

SEQUENCE LISTING

<160> NUMBER OF SEQ ID NOS: 19

<210> SEQ ID NO 1
<211> LENGTH: 20
<212> TYPE: DNA
<213> ORGANISM: Murine Kidney Parvovirus

<400> SEQUENCE: 1
tacatggcca aagatccaca 20

<210> SEQ ID NO 2

```
<211> LENGTH: 20
<212> TYPE: DNA
<213> ORGANISM: Murine Kidney Parvovirus

<400> SEQUENCE: 2
gtggcagtca cccagctaat                                               20

<210> SEQ ID NO 3
<211> LENGTH: 4442
<212> TYPE: DNA
<213> ORGANISM: Murine Kidney Parvovirus
<220> FEATURE:
<221> NAME/KEY: 5'UTR
<222> LOCATION: (1)..(722)
<220> FEATURE:
<221> NAME/KEY: misc_feature
<222> LOCATION: (1)..(52)
<223> OTHER INFORMATION: 5' inverted terminal repeat
<220> FEATURE:
<221> NAME/KEY: misc_feature
<222> LOCATION: (94)..(145)
<223> OTHER INFORMATION: 5' inverted terminal repeat
<220> FEATURE:
<221> NAME/KEY: misc_feature
<222> LOCATION: (723)..(2702)
<223> OTHER INFORMATION: REP gene CDS
<220> FEATURE:
<221> NAME/KEY: misc_feature
<222> LOCATION: (2695)..(4185)
<223> OTHER INFORMATION: VP1 gene CDS
<220> FEATURE:
<221> NAME/KEY: 3'UTR
<222> LOCATION: (4186)..(4354)
<220> FEATURE:
<221> NAME/KEY: misc_feature
<222> LOCATION: (4237)..(4286)
<223> OTHER INFORMATION: 3' inverted terminal repeat
<220> FEATURE:
<221> NAME/KEY: misc_feature
<222> LOCATION: (4305)..(4354)
<223> OTHER INFORMATION: 3' inverted terminal repeat

<400> SEQUENCE: 3
ctacgaaact ggcagggcgc ccgggtagtc ttccacgggg gcggggcctt tgttaacatg    60
tgttaacgtt aacgcacgca gtgcgcgcac atgcaaaggc cccgccccg tggaagacta    120 cccgggcgcc ctgccagttt cgtagcagtc atgtgttgtt gtcctttgtg tggatgtgac   180
tgtggggaca cggaacagaa tattctgatt cgcttgatat gccgggcgga ggtaataaat   240
acaggcagtg gtacgccatg cgcgccagac tccgcgcagc aggcgagtgg gacgcgcatc   300
gggcgggtct gtcgggattg tctgaagcaa ctcgaggagc acaagaagac gtgccagatc   360
ttactgaacc tgatacgcct gactctgcag attcatcagc tgcaaagcga ccgcgtctag   420
aaggagaagg aggtgagtca gaatcggact ctgtaccatc acttgaaggg tctccaactg   480
ccgaaggtaa ttaaaaacct tttttatat cttcttacag atgtctatgt ggtcaggacc    540
tacgggattc tctctcttgc ttattagctc gcatgctaat gctcaagagc tcttggaaga   600
tgctatctgc ctgctctcta accgctggca tatagaattt gagataaaaa accaagataa   660
tgtctggtat gcctggggaa acaaagtag attcaccgta ggggaatcta ctttacaaag    720
agctctcggt gatctctatt cacaggagct tgtcaccttt cagaagggac caccggacac   780
ttcctttgac agcgccctac gctaccaaaa atgcaagcgc aaatggaacg tgcccgacgt   840
agtctctctg ccctcagacg atactggtgg ggcggcaacg cctgtcatca gctttcggaa   900
gaaagcgaga taatttcacc agaaaatcta aacaaatca tgcttaactg ggactctcgg   960
gtatggcaag cctgtgtact gggtatctgg gatactgtac ctgtcagaga tcctagacct  1020
```

```
tattgcttct tactaaccaa tattccttct gttaaaaaat ggttaatttg tgctgaagaa      1080
gatagcaatg aacagactca cattcacctg ttagctctca cctcacagag atcagatgct      1140
tttaagagaa ctttagaaaa aacctggaaa caggtagcta tagtagccat gtcagatata      1200
gaagaaccag atccaaccct agagattgtc aaatgtcaga aatgccacaa accgagtagt      1260
ctgctcgctt acatggccaa agatccacat tggatcgcag ccaatgacat gcaaaccta      1320 ggcatctttg aatctgtcta tgcgcatgac tggggacaga ggttccgaga aaacaaacc      1380 ttagacaaag ctaagaaaac cgatccgacc acctcacaga tgcatactat cacagctgag      1440
atcacagaag tcattatgca acacaactgt aaatcggtag aagactgcat gaaagcagca      1500
cccactgtga ttgctaaaca tttacacaga gccggtttag gcacgattat ccagaattgt      1560
attagctggg tgactgccac aggagggga tggtcacttc ctagtatcgg agccaaacat      1620
ccacccgagc cagaagccat tcatacaatc ttattacacc aaggaatttc accagctgac      1680
tttgatccaa tttttttataa atggttagct aaagaggaaa ctaaaaagaa caccctagtc      1740
ctctggggac ctagcaacac aggaaaaagc gcattcatca gcggcttaaa aacatgtacc      1800
aactggggag aagtcgtaaa ttctaatact tttgcttttg aagctttaat caatgctcaa      1860
ttaggagttt gggaagaacc tctgatctca ccagaactag cggaaaaagc caaacagatc      1920
tttgaaggaa tggaaacctc cattcctgtt aaatatagaa aaccagtcaa actaccacgc      1980
atacctatta ttatcaccac taatcatgct ccctggcgct tctgtactaa agaagaagag      2040
atgtttagaa atagaatgta catttttcacc tggtctcaaa atatgcatga tacaccattt      2100
atttgcagag ctagtgaata tagctgccaa tgccgcgttt gtcaaacaag tcgaggcggc      2160
caggcttgtg ctggtgggca atcagctggc agcttgcaga gaaggaaca atccgtttca      2220 gaattggttc agcccgaacc ctcgtcaagc tatgtttcaa cccgatcctt gcctgtatct      2280
cgagaagaaa caccactacc tgcagcagaa ggtctcggga gccaccacca gcgacattgc      2340
agcagtccag gagggagtc gatcgaacgc acccacagcc aagacctag ctgcagcacc      2400 ggctcctcaa ctagcgacag cctacgaccc agtggggaac acagatccag cgatcccgga      2460
gcaggaatat catgttcctt ctccgggagc cttgagtgtg tggagtcccc tctctctgga      2520
ggagacgatg gagatgatct cccaagagat agaatgggag aacctacaag cccagatagc      2580
tcgacaggta gctcagatat tagcagacct agaggaaaac gcagacatag ccaagaaatg      2640
gtggtgttgg gggaaaccca aagcaaaaaa acacgggatc aggtttcaac cgccgtcaca      2700
ggcatgggta gggatctggg caccttaaat attcctacac gagcacaatg gttcacttat      2760
ctatcttatt tacagaaaca ctatggctga agatgtcacc tttcataaca cctacatggt      2820
ctattggaaa atcaaccct tcatctatcc aaacaccaat atcaatccac caaatgcaca      2880
taccatgtca gccggagcta tcaatactgg atggcatata atcccgacta tcctctggaa      2940
acatttcctc acacccaagc aatggacaga attcactatt aattatgaag catatacagt      3000
taaaggatat tcctgcacca tatataatcc tattcctatg acacaacagc tggcaatcca      3060
aggcactacc gctttcactg ctttcaacaa taccatctat acactaggag cacaagatga      3120
tttatatgaa acagcatatc ataattggta tagtgacgac agcacaggag attacaaagc      3180
tttcaatcta tcatttaaag aaggacagta caaaatctc agtggttcat ggaaaaaac      3240 catatggcca atatactcat ggagaacaga aaatgcccga aatgcctctt cttccaccta      3300
ctcatatctc aatggtatag atagttatgc agtatggcca agaacaaaag acaaagagtt      3360
```

-continued

```
aataccaaca ggggtattct gggatccatt aaacgatgca atgggatat tggaattaag   3420 acctggaaag aattctatgt ccttctcctg ggaacaacat ccctgtgatg aaaataaatg   3480
gtttaacatt gatcaaattg caaagtggtt tccttacacc gtcgatacac cttatctaaa   3540
cccacaaacc tatggtccac ccggttccta taaactatat ggggaagacg atcctgatca   3600
actcaccaca cctagttcct ggacggccta cagtgccaaa atgactaca ccatacctaa    3660 tctgctcgac atgccaatag tacccatgca atggttctgg caagaaatcc agaaatccat   3720
tgcagaagtt ccagatgtca aaaacccat gctatactgg gcaggcacag aatatgaatg    3780
ctataaatat ggacctacac aatgcttcct caaaggcatt ccattattcg atgataatga   3840
cacccatgta gccaccacca cacaaggctg tttcaggatc agtctacacc tagcggggaa   3900
aaaaagacgc agccgcatct atgcaccaac atggggtcca ctctcctgga acaatgcta    3960 tgccaccgac acgccattcg ctcccagcat ggtcagatac agaacaggag gagcgagaag   4020
aacgtggaca aatatcaaca gagatgcaga aggagtccac aaagatttcc actacagaga   4080
agatccatat gatatcacct caaccgtccc agacaccaga ggaacggcaa cagtcaccga   4140
cagtaaagcc accatgcacc catatgaaca agcagcctcc ggcatgtacc tcaaccataa   4200
ggaaatgaga caagtccgcg cagccgcaga agcaacacga tctcaacctg ctgtagccat   4260
gcaaactcaa taaaaagtcc ctgtgtcctt acaaaccaca tccacacaat acaaaatctt   4320
attgttaacc cgcctcccaa tcttggcttc acttcctgaa ccccgggggcg gcccagtcgt   4380 acagaacatg tggggccgcc ccggggttca ggaagtgaag ccaagattgg gaggcgggtt   4440
aa                                                                 4442
```

<210> SEQ ID NO 4
<211> LENGTH: 659
<212> TYPE: PRT
<213> ORGANISM: Murine Kidney Parvovirus

<400> SEQUENCE: 4

```
Met Gln Ala Gln Met Glu Arg Ala Arg Arg Ser Leu Ser Ala Leu Arg
1               5                   10                  15

Arg Tyr Trp Trp Gly Gly Asn Ala Cys His Gln Leu Ser Glu Glu Ser
            20                  25                  30

Glu Ile Ile Ser Pro Glu Asn Leu Lys Gln Ile Met Leu Asn Trp Asp
        35                  40                  45

Ser Arg Val Trp Gln Ala Cys Val Leu Gly Ile Trp Asp Thr Val Pro
    50                  55                  60

Val Arg Asp Pro Arg Pro Tyr Cys Phe Leu Leu Thr Asn Ile Pro Ser
65                  70                  75                  80

Val Lys Lys Trp Leu Ile Cys Ala Glu Glu Asp Ser Asn Glu Gln Thr
                85                  90                  95

His Ile His Leu Leu Ala Leu Thr Ser Gln Arg Ser Asp Ala Phe Lys
            100                 105                 110

Arg Thr Leu Glu Lys Thr Trp Lys Gln Val Ala Ile Ala Met Ser
        115                 120                 125

Asp Ile Glu Glu Pro Asp Pro Thr Leu Glu Ile Val Lys Cys Gln Lys
    130                 135                 140

Cys His Lys Pro Ser Ser Leu Leu Ala Tyr Met Ala Lys Asp Pro His
145                 150                 155                 160

Trp Ile Ala Ala Asn Asp Met Gln Thr Leu Gly Ile Phe Glu Ser Val
                165                 170                 175
```

-continued

```
Tyr Ala His Asp Trp Gly Gln Arg Phe Arg Glu Lys Gln Thr Leu Asp
            180                 185                 190

Lys Ala Lys Lys Thr Asp Pro Thr Thr Ser Gln Met His Thr Ile Thr
        195                 200                 205

Ala Glu Ile Thr Glu Val Ile Met Gln His Asn Cys Lys Ser Val Glu
    210                 215                 220

Asp Cys Met Lys Ala Ala Pro Thr Val Ile Ala Lys His Leu His Arg
225                 230                 235                 240

Ala Gly Leu Gly Thr Ile Ile Gln Asn Cys Ile Ser Trp Val Thr Ala
                245                 250                 255

Thr Gly Gly Gly Trp Ser Leu Pro Ser Ile Gly Ala Lys His Pro Pro
            260                 265                 270

Glu Pro Glu Ala Ile His Thr Ile Leu Leu His Gln Gly Ile Ser Pro
        275                 280                 285

Ala Asp Phe Asp Pro Ile Phe Tyr Lys Trp Leu Ala Lys Glu Glu Thr
    290                 295                 300

Lys Lys Asn Thr Leu Val Leu Trp Gly Pro Ser Asn Thr Gly Lys Ser
305                 310                 315                 320

Ala Phe Ile Ser Gly Leu Lys Thr Cys Thr Asn Trp Gly Glu Val Val
                325                 330                 335

Asn Ser Asn Thr Phe Ala Phe Glu Ala Leu Ile Asn Ala Gln Leu Gly
            340                 345                 350

Val Trp Glu Glu Pro Leu Ile Ser Pro Glu Leu Ala Glu Lys Ala Lys
        355                 360                 365

Gln Ile Phe Glu Gly Met Glu Thr Ser Ile Pro Val Lys Tyr Arg Lys
    370                 375                 380

Pro Val Lys Leu Pro Arg Ile Pro Ile Ile Thr Thr Asn His Ala
385                 390                 395                 400

Pro Trp Arg Phe Cys Thr Lys Glu Glu Glu Met Phe Arg Asn Arg Met
                405                 410                 415

Tyr Ile Phe Thr Trp Ser Gln Asn Met His Asp Thr Pro Phe Ile Cys
            420                 425                 430

Arg Ala Ser Glu Tyr Ser Cys Gln Cys Arg Val Cys Gln Thr Ser Arg
        435                 440                 445

Gly Gly Gln Ala Cys Ala Gly Gly Gln Ser Ala Gly Ser Leu Gln Arg
    450                 455                 460

Lys Glu Gln Ser Val Ser Glu Leu Val Gln Pro Glu Pro Ser Ser Ser
465                 470                 475                 480

Tyr Val Ser Thr Arg Ser Leu Pro Val Ser Arg Glu Glu Thr Pro Leu
                485                 490                 495

Pro Ala Ala Glu Gly Leu Gly Ser His His Gln Arg His Cys Ser Ser
            500                 505                 510

Pro Gly Gly Glu Ser Ile Glu Arg Thr His Ser Pro Arg Pro Ser Cys
        515                 520                 525

Ser Thr Gly Ser Ser Thr Ser Asp Ser Leu Arg Pro Ser Gly Glu His
    530                 535                 540

Arg Ser Ser Asp Pro Gly Ala Gly Ile Ser Cys Ser Phe Ser Gly Ser
545                 550                 555                 560

Leu Glu Cys Val Glu Ser Pro Leu Ser Gly Gly Asp Asp Gly Asp Asp
                565                 570                 575

Leu Pro Arg Asp Arg Met Gly Glu Pro Thr Ser Pro Asp Ser Ser Thr
            580                 585                 590

Gly Ser Ser Asp Ile Ser Arg Pro Arg Gly Lys Arg Arg His Ser Gln
```

```
                    595                 600                 605
Glu Met Val Val Leu Gly Glu Thr Gln Ser Lys Lys Thr Arg Asp Gln
    610                 615                 620

Val Ser Thr Ala Val Thr Gly Met Gly Arg Asp Leu Gly Thr Leu Asn
625                 630                 635                 640

Ile Pro Thr Arg Ala Gln Trp Phe Thr Tyr Leu Ser Tyr Leu Gln Lys
                645                 650                 655

His Tyr Gly

<210> SEQ ID NO 5
<211> LENGTH: 295
<212> TYPE: PRT
<213> ORGANISM: Murine Kidney Parvovirus

<400> SEQUENCE: 5

Met Pro Gly Gly Gly Asn Lys Tyr Arg Gln Trp Tyr Ala Met Arg Ala
1               5                   10                  15

Arg Leu Arg Ala Ala Gly Glu Trp Asp Ala His Arg Ala Gly Leu Ser
            20                  25                  30

Gly Leu Ser Glu Ala Thr Arg Gly Ala Gln Glu Asp Val Pro Asp Leu
        35                  40                  45

Thr Glu Pro Asp Thr Pro Asp Ser Ala Asp Ser Ser Ala Ala Lys Arg
    50                  55                  60

Pro Arg Leu Glu Gly Glu Gly Gly Glu Ser Glu Ser Asp Ser Val Pro
65                  70                  75                  80

Ser Leu Glu Gly Ser Pro Thr Ala Glu Glu Leu Val Asn Ile Ala Ala
                85                  90                  95

Asn Ala Ala Phe Val Lys Gln Val Glu Ala Ala Arg Leu Val Leu Val
            100                 105                 110

Gly Asn Gln Leu Ala Ala Cys Arg Glu Arg Asn Asn Pro Phe Gln Asn
        115                 120                 125

Trp Phe Ser Pro Asn Pro Arg Gln Ala Met Phe Gln Pro Asp Pro Cys
    130                 135                 140

Leu Tyr Leu Glu Lys Lys His His Tyr Leu Gln Gln Lys Val Ser Gly
145                 150                 155                 160

Ala Thr Thr Ser Asp Ile Ala Ala Val Gln Glu Gly Ser Arg Ser Asn
                165                 170                 175

Ala Pro Thr Ala Gln Asp Leu Ala Ala Ala Pro Ala Pro Gln Leu Ala
            180                 185                 190

Thr Ala Tyr Asp Pro Val Gly Asn Thr Asp Pro Ala Ile Pro Glu Gln
        195                 200                 205

Glu Tyr His Val Pro Ser Pro Gly Ala Leu Ser Val Trp Ser Pro Leu
    210                 215                 220

Ser Leu Glu Glu Thr Met Glu Met Ile Ser Gln Glu Ile Glu Trp Glu
225                 230                 235                 240

Asn Leu Gln Ala Gln Ile Ala Arg Gln Val Ala Gln Ile Leu Ala Asp
                245                 250                 255

Leu Glu Glu Asn Ala Asp Ile Ala Lys Lys Trp Trp Cys Trp Gly Lys
            260                 265                 270

Pro Lys Ala Lys Lys His Gly Ile Arg Phe Gln Pro Pro Ser Gln Ala
        275                 280                 285

Trp Val Gly Ile Trp Ala Pro
    290                 295
```

-continued

```
<210> SEQ ID NO 6
<211> LENGTH: 240
<212> TYPE: PRT
<213> ORGANISM: Murine Kidney Parvovirus

<400> SEQUENCE: 6

Met Leu Pro Gly Ala Ser Val Leu Lys Lys Arg Cys Leu Glu Ile
1               5                   10                  15

Glu Cys Thr Phe Ser Pro Gly Leu Lys Ile Cys Met Ile His His Leu
            20                  25                  30

Phe Ala Glu Leu Val Asn Ile Ala Ala Asn Ala Ala Phe Val Lys Gln
        35                  40                  45

Val Glu Ala Ala Arg Leu Val Leu Val Gly Asn Gln Leu Ala Ala Cys
    50                  55                  60

Arg Glu Arg Asn Asn Pro Phe Gln Asn Trp Phe Ser Pro Asn Pro Arg
65                  70                  75                  80

Gln Ala Met Phe Gln Pro Asp Pro Cys Leu Tyr Leu Glu Lys Lys His
                85                  90                  95

His Tyr Leu Gln Gln Lys Val Ser Gly Ala Thr Thr Ser Asp Ile Ala
            100                 105                 110

Ala Val Gln Glu Gly Ser Arg Ser Asn Ala Pro Thr Ala Gln Asp Leu
        115                 120                 125

Ala Ala Ala Pro Ala Pro Gln Leu Ala Thr Ala Tyr Asp Pro Val Gly
    130                 135                 140

Asn Thr Asp Pro Ala Ile Pro Glu Gln Glu Tyr His Val Pro Ser Pro
145                 150                 155                 160

Gly Ala Leu Ser Val Trp Ser Pro Leu Ser Leu Glu Glu Thr Met Glu
                165                 170                 175

Met Ile Ser Gln Glu Ile Glu Trp Glu Asn Leu Gln Ala Gln Ile Ala
            180                 185                 190

Arg Gln Val Ala Gln Ile Leu Ala Asp Leu Glu Glu Asn Ala Asp Ile
        195                 200                 205

Ala Lys Lys Trp Trp Cys Trp Gly Lys Pro Lys Ala Lys Lys His Gly
    210                 215                 220

Ile Arg Phe Gln Pro Pro Ser Gln Ala Trp Val Gly Ile Trp Ala Pro
225                 230                 235                 240

<210> SEQ ID NO 7
<211> LENGTH: 213
<212> TYPE: PRT
<213> ORGANISM: Murine Kidney Parvovirus

<400> SEQUENCE: 7

Met Ile His His Leu Phe Ala Glu Leu Val Asn Ile Ala Ala Asn Ala
1               5                   10                  15

Ala Phe Val Lys Gln Val Glu Ala Ala Arg Leu Val Leu Val Gly Asn
            20                  25                  30

Gln Leu Ala Ala Cys Arg Glu Arg Asn Asn Pro Phe Gln Asn Trp Phe
        35                  40                  45

Ser Pro Asn Pro Arg Gln Ala Met Phe Gln Pro Asp Pro Cys Leu Tyr
    50                  55                  60

Leu Glu Lys Lys His His Tyr Leu Gln Gln Lys Val Ser Gly Ala Thr
65                  70                  75                  80

Thr Ser Asp Ile Ala Ala Val Gln Glu Gly Ser Arg Ser Asn Ala Pro
                85                  90                  95

Thr Ala Gln Asp Leu Ala Ala Ala Pro Ala Pro Gln Leu Ala Thr Ala
```

```
              100                 105                 110
Tyr Asp Pro Val Gly Asn Thr Asp Pro Ala Ile Pro Glu Gln Glu Tyr
            115                 120                 125

His Val Pro Ser Pro Gly Ala Leu Ser Val Trp Ser Pro Leu Ser Leu
        130                 135                 140

Glu Glu Thr Met Glu Met Ile Ser Gln Glu Ile Glu Trp Glu Asn Leu
145                 150                 155                 160

Gln Ala Gln Ile Ala Arg Gln Val Ala Gln Ile Leu Ala Asp Leu Glu
                165                 170                 175

Glu Asn Ala Asp Ile Ala Lys Lys Trp Trp Cys Trp Gly Lys Pro Lys
            180                 185                 190

Ala Lys Lys His Gly Ile Arg Phe Gln Pro Pro Ser Gln Ala Trp Val
        195                 200                 205

Gly Ile Trp Ala Pro
    210

<210> SEQ ID NO 8
<211> LENGTH: 496
<212> TYPE: PRT
<213> ORGANISM: Murine Kidney Parvovirus

<400> SEQUENCE: 8

Met Ala Glu Asp Val Thr Phe His Asn Thr Tyr Met Val Tyr Trp Lys
1               5                   10                  15

Asn Gln Pro Phe Ile Tyr Pro Asn Thr Asn Ile Asn Pro Pro Asn Ala
            20                  25                  30

His Thr Met Ser Ala Gly Ala Ile Asn Thr Gly Trp His Ile Ile Pro
        35                  40                  45

Thr Ile Leu Trp Lys His Phe Leu Thr Pro Lys Gln Trp Thr Glu Phe
    50                  55                  60

Thr Ile Asn Tyr Glu Ala Tyr Thr Val Lys Gly Tyr Ser Cys Thr Ile
65              70                  75                  80

Tyr Asn Pro Ile Pro Met Thr Gln Gln Leu Ala Ile Gln Gly Thr Thr
                85                  90                  95

Ala Phe Thr Ala Phe Asn Asn Thr Ile Tyr Thr Leu Gly Ala Gln Asp
            100                 105                 110

Asp Leu Tyr Glu Thr Ala Tyr His Asn Trp Tyr Ser Asp Asp Ser Thr
        115                 120                 125

Gly Asp Tyr Lys Ala Phe Asn Leu Ser Phe Lys Glu Gly Gln Tyr Lys
    130                 135                 140

Asn Leu Ser Gly Ser Trp Lys Lys Thr Ile Trp Pro Ile Tyr Ser Trp
145                 150                 155                 160

Arg Thr Glu Asn Ala Arg Asn Ala Ser Ser Thr Tyr Ser Tyr Leu
                165                 170                 175

Asn Gly Ile Asp Ser Tyr Ala Val Trp Pro Arg Thr Lys Asp Lys Glu
            180                 185                 190

Leu Ile Pro Thr Gly Val Phe Trp Asp Pro Leu Asn Asp Ala Asn Gly
        195                 200                 205

Ile Leu Glu Leu Arg Pro Gly Lys Asn Ser Met Ser Phe Ser Trp Glu
    210                 215                 220

Gln His Pro Cys Asp Glu Asn Lys Trp Phe Asn Ile Asp Gln Ile Ala
225                 230                 235                 240

Lys Trp Phe Pro Tyr Thr Val Asp Thr Pro Tyr Leu Asn Pro Gln Thr
                245                 250                 255
```

```
Tyr Gly Pro Pro Gly Ser Tyr Lys Leu Tyr Gly Glu Asp Pro Asp
            260                 265                 270

Gln Leu Thr Thr Pro Ser Ser Trp Thr Ala Tyr Ser Ala Lys Asn Asp
            275                 280                 285

Tyr Thr Ile Pro Asn Leu Leu Asp Met Pro Ile Val Pro Met Gln Trp
        290                 295                 300

Phe Trp Gln Glu Ile Gln Lys Ser Ile Ala Glu Val Pro Asp Val Lys
305                 310                 315                 320

Lys Pro Met Leu Tyr Trp Ala Gly Thr Glu Tyr Glu Cys Tyr Lys Tyr
                325                 330                 335

Gly Pro Thr Gln Cys Phe Leu Lys Gly Ile Pro Leu Phe Asp Asp Asn
            340                 345                 350

Asp Thr His Val Ala Thr Thr Thr Gln Gly Cys Phe Arg Ile Ser Leu
        355                 360                 365

His Leu Ala Gly Lys Lys Arg Arg Ser Arg Ile Tyr Ala Pro Thr Trp
    370                 375                 380

Gly Pro Leu Ser Trp Arg Gln Cys Tyr Ala Thr Asp Thr Pro Phe Ala
385                 390                 395                 400

Pro Ser Met Val Arg Tyr Arg Thr Gly Gly Ala Arg Arg Thr Trp Thr
                405                 410                 415

Asn Ile Asn Arg Asp Ala Glu Gly Val His Lys Asp Phe His Tyr Arg
            420                 425                 430

Glu Asp Pro Tyr Asp Ile Thr Ser Thr Val Pro Asp Thr Arg Gly Thr
        435                 440                 445

Ala Thr Val Thr Asp Ser Lys Ala Thr Met His Pro Tyr Glu Gln Ala
    450                 455                 460

Ala Ser Gly Met Tyr Leu Asn His Lys Glu Met Arg Gln Val Arg Ala
465                 470                 475                 480

Ala Ala Glu Ala Thr Arg Ser Gln Pro Ala Val Ala Met Gln Thr Gln
                485                 490                 495

<210> SEQ ID NO 9
<211> LENGTH: 1980
<212> TYPE: DNA
<213> ORGANISM: Murine Kidney Parvovirus

<400> SEQUENCE: 9
atgcaagcgc aaatggaacg tgcccgacgt agtctctctg ccctcagacg atactggtgg    60
ggcggcaacg cctgtcatca gctttcggaa gaaagcgaga taatttcacc agaaaatcta   120
aaacaaatca tgcttaactg ggactctcgg gtatggcaag cctgtgtact gggtatctgg   180
gatactgtac ctgtcagaga tcctagacct tattgcttct tactaaccaa tattccttct   240
gttaaaaaat ggttaatttg tgctgaagaa gatagcaatg aacagactca cattcacctg   300
ttagctctca cctcacagag atcagatgct tttaagagaa ctttagaaaa aacctggaaa   360
caggtagcta tagtagccat gtcagatata aagaaccag atccaacctt agagattgtc   420
aaatgtcaga atgccacaa accgagtagt ctgctcgctt acatggccaa agatccacat   480
tggatcgcag ccaatgacat gcaaaccta ggcatctttg aatctgtcta tgcgcatgac   540
tggggacaga ggttccgaga aaaacaaacc ttagacaaag ctaagaaaac cgatccgacc   600
acctcacaga tgcatactat cacagctgag atcacagaag tcattatgca cacaactgt   660 aaatcggtag aagactgcat gaaagcagca cccactgtga ttgctaaaca tttacagaa   720 gccggtttag gcacgattat ccagaattgt attagctggg tgactgccac aggagggga   780
```

-continued

| | |
|---|---|
| tggtcacttc ctagtatcgg agccaaacat ccacccgagc cagaagccat tcatacaatc | 840 |
| ttattcacc aaggaatttc accagctgac tttgatccaa tttttttataa atggttagct | 900 |
| aaagaggaaa ctaaaaagaa caccctagtc ctctggggac ctagcaacac aggaaaaagc | 960 |
| gcattcatca gcggcttaaa aacatgtacc aactggggag aagtcgtaaa ttctaatact | 1020 |
| tttgcttttg aagctttaat caatgctcaa ttaggagttt gggaagaacc tctgatctca | 1080 |
| ccagaactag cggaaaaagc caaacagatc tttgaaggaa tggaaacctc cattcctgtt | 1140 |
| aaatatagaa aaccagtcaa actaccacgc atacctatta ttatcaccac taatcatgct | 1200 |
| ccctggcgct tctgtactaa agaagaagag atgtttagaa atagaatgta cattttcacc | 1260 |
| tggtctcaaa atatgcatga tacaccattt atttgcagag ctagtgaata tagctgccaa | 1320 |
| tgccgcgttt gtcaaacaag tcgaggcggc caggcttgtg ctggtgggca atcagctggc | 1380 |
| agcttgcaga gaaaggaaca atccgtttca gaattggttc agcccgaacc ctcgtcaagc | 1440 |
| tatgtttcaa cccgatcctt gcctgtatct cgagaagaaa caccactacc tgcagcagaa | 1500 |
| ggtctcggga gccaccacca gcgacattgc agcagtccag gagggagtc gatcgaacgc | 1560 |
| acccacagcc caagacctag ctgcagcacc ggctcctcaa ctagcgacag cctacgaccc | 1620 |
| agtggggaac acagatccag cgatcccgga gcaggaatat catgttcctt ctccgggagc | 1680 |
| cttgagtgtg tggagtcccc tctctctgga ggagacgatg gagatgatct cccaagagat | 1740 |
| agaatgggag aacctacaag cccagatagc tcgacaggta gctcagatat tagcagacct | 1800 |
| agaggaaaac gcagacatag ccaagaaatg gtggtgttgg gggaaaccca agcaaaaaa | 1860 |
| acacgggatc aggtttcaac cgccgtcaca ggcatgggta gggatctggg caccttaaat | 1920 |
| attcctacac gagcacaatg gttcacttat ctatcttatt tacagaaaca ctatggctga | 1980 |

<210> SEQ ID NO 10
<211> LENGTH: 888
<212> TYPE: DNA
<213> ORGANISM: Murine Kidney Parvovirus

<400> SEQUENCE: 10

| | |
|---|---|
| atgccgggcg gaggtaataa atacaggcag tggtacgcca tgcgcgccag actccgcgca | 60 |
| gcaggcgagt gggacgcgca tcgggcgggt ctgtcgggat tgtctgaagc aactcgagga | 120 |
| gcacaagaag acgtgccaga tcttactgaa cctgatacgc ctgactctgc agattcatca | 180 |
| gctgcaaagc gaccgcgtct agaaggagaa ggaggtgagt cagaatcgga ctctgtacca | 240 |
| tcacttgaag ggtctccaac tgccgaagag ctagtgaata tagctgccaa tgccgcgttt | 300 |
| gtcaaacaag tcgaggcggc caggcttgtg ctggtgggca atcagctggc agcttgcaga | 360 |
| gaaaggaaca atccgtttca gaattggttc agcccgaacc ctcgtcaagc tatgtttcaa | 420 |
| cccgatcctt gcctgtatct cgagaagaaa caccactacc tgcagcagaa ggtctcggga | 480 |
| gccaccacca gcgacattgc agcagtccag gagggagtc gatcgaacgc acccacagcc | 540 |
| caagacctag ctgcagcacc ggctcctcaa ctagcgacag cctacgaccc agtggggaac | 600 |
| acagatccag cgatcccgga gcaggaatat catgttcctt ctccgggagc cttgagtgtg | 660 |
| tggagtcccc tctctctgga ggagacgatg gagatgatct cccaagagat agaatgggag | 720 |
| aacctacaag cccagatagc tcgacaggta gctcagatat tagcagacct agaggaaaac | 780 |
| gcagacatag ccaagaaatg gtggtgttgg gggaaaccca agcaaaaaa acacgggatc | 840 |
| aggtttcaac cgccgtcaca ggcatgggta gggatctggg caccttaa | 888 |

<210> SEQ ID NO 11
<211> LENGTH: 723
<212> TYPE: DNA
<213> ORGANISM: Murine Kidney Parvovirus

<400> SEQUENCE: 11

| | | | | | |
|---|---|---|---|---|---|
| atgctccctg | gcgcttctgt | actaaagaag | aagagatgtt | tagaaataga | atgtacattt | 60 |
| tcacctggtc | tcaaaatatg | catgatacac | catttatttg | cagagctagt | gaatatagct | 120 |
| gccaatgccg | cgtttgtcaa | acaagtcgag | gcggccaggc | ttgtgctggt | gggcaatcag | 180 |
| ctggcagctt | gcagagaaag | gaacaatccg | tttcagaatt | ggttcagccc | gaaccctcgt | 240 |
| caagctatgt | ttcaacccga | tccttgcctg | tatctcgaga | agaaacacca | ctacctgcag | 300 |
| cagaaggtct | cgggagccac | caccagcgac | attgcagcag | tccaggaggg | gagtcgatcg | 360 |
| aacgcaccca | cagcccaaga | cctagctgca | gcaccggctc | ctcaactagc | gacagcctac | 420 |
| gacccagtgg | ggaacacaga | tccagcgatc | ccggagcagg | aatatcatgt | tccttctccg | 480 |
| ggagccttga | gtgtgtggag | tcccctctct | ctggaggaga | cgatggagat | gatctcccaa | 540 |
| gagatagaat | gggagaacct | acaagcccag | atagctcgac | aggtagctca | gatattagca | 600 |
| gacctagagg | aaaacgcaga | catagccaag | aaatggtggt | gttggggggaa | acccaaagca | 660 |
| aaaaaacacg | ggatcaggtt | tcaaccgccg | tcacaggcat | gggtagggat | ctgggcacct | 720 |
| taa | | | | | | 723 |

<210> SEQ ID NO 12
<211> LENGTH: 688
<212> TYPE: DNA
<213> ORGANISM: Murine Kidney Parvovirus

<400> SEQUENCE: 12

| | | | | | |
|---|---|---|---|---|---|
| atgtttagaa | atagaatgta | cattttcacc | tggtctcaaa | atatgcatga | tacaccattt | 60 |
| atttgcagag | ctagtgaata | tagctgccaa | tgccgcgttt | gtcaaacaag | tcgaggcggc | 120 |
| caggcttgtg | ctggtgggca | atcagctggc | agcttgcaga | gaaaggaaca | atccgtttca | 180 |
| gaattggttc | agcccgaacc | ctcgtcaagc | tatgtttcaa | cccgatcctt | gcctgtatct | 240 |
| cgagaagaaa | caccactacc | tgcagcagaa | ggtctcggga | gccaccacca | gcgacattgc | 300 |
| agcagtccag | gaggggagtc | gatcgaacgc | acccacagcc | caagacctag | ctgcagcacc | 360 |
| ggctcctcaa | ctagcgacag | cctacgaccc | agtggggaac | acagatccag | cgatcccgga | 420 |
| gcaggaatat | catgttcctt | ctccgggagc | cttgagtgtg | tggagtcccc | tctctctgga | 480 |
| ggagacgatg | gagatgatct | cccaagagat | agaatgggag | aacctacaag | cccagatagc | 540 |
| tcgacaggta | gctcagatat | tagcagacct | agaggaaaac | gcagacatag | ccaagaaatg | 600 |
| gtggtgttgg | gggaaaccca | aagcaaaaaa | acacgggatc | aggtttcaac | cgccgtcaca | 660 |
| ggcatgggta | gggatctggg | caccttaa | | | | 688 |

<210> SEQ ID NO 13
<211> LENGTH: 1491
<212> TYPE: DNA
<213> ORGANISM: Murine Kidney Parvovirus

<400> SEQUENCE: 13

| | | | | | |
|---|---|---|---|---|---|
| atggctgaag | atgtcacctt | tcataacacc | tacatggtct | attggaaaaa | tcaacccttc | 60 |
| atctatccaa | acaccaatat | caatccacca | aatgcacata | ccatgtcagc | cggagctatc | 120 |
| aatactggat | ggcatataat | cccgactatc | ctctggaaac | atttcctcac | acccaagcaa | 180 |

```
tggacagaat tcactattaa ttatgaagca tatacagtta aaggatattc ctgcaccata    240
tataatccta ttcctatgac acaacagctg gcaatccaag gcactaccgc tttcactgct    300
ttcaacaata ccatctatac actaggagca caagatgatt tatatgaaac agcatatcat    360
aattggtata gtgacgacag cacaggagat tacaaagctt tcaatctatc atttaaagaa    420
ggacagtaca aaaatctcag tggttcatgg aaaaaaacca tatggccaat atactcatgg    480
agaacagaaa atgcccgaaa tgcctcttct tccacctact catatctcaa tggtatagat    540
agttatgcag tatggccaag aacaaaagac aaagagttaa taccaacagg ggtattctgg    600
gatccattaa acgatgcaaa tgggatattg gaattaagac ctggaaagaa ttctatgtcc    660
ttctcctggg aacaacatcc ctgtgatgaa aataaatggt ttaacattga tcaaattgca    720
aagtggtttc cttacaccgt cgatacacct tatctaaacc cacaaaccta tggtccaccc    780
ggttcctata aactatatgg ggaagacgat cctgatcaac tcaccacacc tagttcctgg    840
acggcctaca gtgccaaaaa tgactacacc ataccta atc tgctcgacat gccaatagta    900
cccatgcaat ggttctggca agaaatccag aaatccattg cagaagttcc agatgtcaaa    960
aaacccatgc tatactgggc aggcacagaa tatgaatgct ataaatatgg acctacacaa   1020
tgcttcctca aaggcattcc attattcgat gataatgaca cccatgtagc caccaccaca   1080
caaggctgtt tcaggatcag tctacaccta gcggggaaaa aaagacgcag ccgcatctat   1140
gcaccaacat ggggtccact ctcctggaga caatgctatg ccaccgacac gccattcgct   1200
cccagcatgg tcagatacag aacaggagga gcgagaagaa cgtggacaaa tatcaacaga   1260
gatgcagaag gagtccacaa agatttccac tacagagaag atccatatga tatcacctca   1320
accgtcccag acaccagagg aacggcaaca gtcaccgaca gtaaagccac catgcaccca   1380
tatgaacaag cagcctccgg catgtacctc aaccataagg aaatgagaca agtccgcgca   1440
gccgcagaag caacacgatc tcaacctgct gtagccatgc aaactcaata a           1491
```

<210> SEQ ID NO 14
<211> LENGTH: 18
<212> TYPE: PRT
<213> ORGANISM: Murine Kidney Parvovirus

<400> SEQUENCE: 14

Thr His Val Ala Thr Thr Thr Gln Gly Cys Phe Arg Ile Ser Leu His
1               5                   10                  15

Leu Ala

<210> SEQ ID NO 15
<211> LENGTH: 672
<212> TYPE: PRT
<213> ORGANISM: Mouse parvovirus 1

<400> SEQUENCE: 15

Met Ala Gly Asn Ala Tyr Ser Asp Glu Val Leu Gly Thr Thr Asn Trp
1               5                   10                  15

Leu Lys Glu Lys Ser Asn Gln Glu Val Phe Ser Phe Val Phe Lys Thr
                20                  25                  30

Glu Asp Val Gln Leu Asn Gly Lys Asp Ile Gly Trp Asn Asn Tyr Lys
            35                  40                  45

Lys Glu Leu Gln Glu Asp Glu Leu Lys Ser Leu Gln Arg Gly Ala Glu
        50                  55                  60

Thr Thr Trp Asp Gln Ser Glu Asp Met Glu Trp Glu Ser Thr Val Asp
65                  70                  75                  80

```
Glu Met Thr Lys Lys Gln Val Phe Ile Tyr Asp Ser Leu Val Lys Lys
                 85                  90                  95

Cys Leu Phe Glu Val Leu Ser Thr Lys Asn Ile Ala Pro Ala Asp Val
                100                 105                 110

Thr Trp Phe Val Gln His Glu Trp Gly Lys Asp Gln Gly Trp His Cys
                115                 120                 125

His Val Leu Ile Gly Gly Lys Asp Phe Ser Gln Ala Gln Gly Lys Trp
            130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Ser Glu Trp Val Thr Leu Leu Thr Tyr Lys His Lys Gln
                180                 185                 190

Thr Lys Lys Asp Tyr Thr Lys Cys Val Leu Phe Gly Asn Met Ile Ala
            195                 200                 205

Tyr Tyr Phe Leu Thr Lys Lys Ile Ser Thr Ser Pro Pro Arg Asp
            210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Asp Met
                245                 250                 255

Arg Pro Glu Thr Val Glu Thr Val Thr Thr Ala Gln Glu Thr Lys
                260                 265                 270

Arg Gly Arg Ile Gln Thr Lys Lys Glu Val Ser Ile Lys Thr Thr Leu
            275                 280                 285

Lys Glu Leu Val His Lys Arg Val Thr Ser Pro Glu Asp Trp Met Met
290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Thr Cys Lys Ile Phe Ala
            355                 360                 365

Phe His Gly Trp Asn Tyr Ile Lys Val Cys His Ala Ile Cys Cys Val
    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
            435                 440                 445

Gly Gln Gln Val Asn Gln Phe Lys Ala Ile Cys Ser Gly Gln Thr Ile
        450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Lys Ile Gly Cys
                485                 490                 495
```

```
Glu Glu Arg Pro Glu His Thr Gln Pro Ile Arg Asp Arg Met Leu Asn
            500                 505                 510

Ile His Leu Thr His Thr Leu Pro Gly Asp Phe Gly Leu Val Asp Lys
        515                 520                 525

Asn Glu Trp Pro Met Ile Cys Ala Trp Leu Val Lys Asn Gly Tyr Gln
    530                 535                 540

Ser Thr Met Ala Ser Tyr Cys Ala Lys Trp Gly Lys Val Pro Asp Trp
545                 550                 555                 560

Thr Glu Asn Trp Ala Glu Pro Lys Val Pro Thr Pro Ile Asn Ser Leu
                565                 570                 575

Gly Ser Ala Arg Ser Pro Phe Thr Thr Pro Lys Ser Thr Pro Leu Ser
            580                 585                 590

Gln Asn Tyr Ala Leu Thr Pro Leu Ala Ser Asp Leu Glu Asp Leu Ala
        595                 600                 605

Leu Glu Pro Trp Ser Thr Pro Asn Thr Pro Val Ala Gly Thr Ala Glu
    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                645                 650                 655

Gly Ala Glu Pro Leu Lys Lys Asp Phe Ser Glu Pro Leu Asn Leu Asp
            660                 665                 670

<210> SEQ ID NO 16
<211> LENGTH: 721
<212> TYPE: PRT
<213> ORGANISM: Minute virus of mice

<400> SEQUENCE: 16

Met Ile Ser Gly Ser Gly Ser Leu Asn Gln Gly Ala Lys Arg Lys Trp
1               5                   10                  15

Ala Trp Phe Lys Val Tyr Lys Gln Leu Leu Lys Ser Val Thr Tyr Leu
            20                  25                  30

Phe Phe His Ser Val Ser Arg Asp Ala Gln Lys Glu Ser Asn Gln Leu
        35                  40                  45

Thr Met Ala Gly Asn Ala Tyr Ser Asp Glu Val Leu Gly Ala Thr Asn
    50                  55                  60

Trp Leu Lys Glu Lys Ser Asn Gln Glu Val Phe Ser Phe Val Phe Lys
65                  70                  75                  80

Asn Glu Asn Val Gln Leu Asn Gly Lys Asp Ile Gly Trp Asn Ser Tyr
                85                  90                  95

Lys Lys Glu Leu Gln Glu Asp Glu Leu Lys Ser Leu Gln Arg Gly Ala
            100                 105                 110

Glu Thr Thr Trp Asp Gln Ser Glu Asp Met Glu Trp Glu Thr Thr Val
        115                 120                 125

Asp Glu Met Thr Lys Lys Gln Val Phe Ile Phe Asp Ser Leu Val Lys
    130                 135                 140

Lys Cys Leu Phe Glu Val Leu Asn Thr Lys Asn Ile Phe Pro Gly Asp
145                 150                 155                 160

Val Asn Trp Phe Val Gln His Glu Trp Gly Lys Asp Gln Gly Trp His
                165                 170                 175

Cys His Val Leu Ile Gly Gly Lys Asp Phe Ser Gln Ala Gln Gly Lys
            180                 185                 190

Trp Trp Arg Arg Gln Leu Asn Val Tyr Trp Ser Arg Trp Leu Val Thr
        195                 200                 205
```

```
Ala Cys Asn Val Gln Leu Thr Pro Ala Glu Arg Ile Lys Leu Arg Glu
    210                 215                 220
Ile Ala Glu Asp Asn Glu Trp Val Thr Leu Leu Thr Tyr Lys His Lys
225                 230                 235                 240
Gln Thr Lys Lys Asp Tyr Thr Lys Cys Val Leu Phe Gly Asn Met Ile
                245                 250                 255
Ala Tyr Tyr Phe Leu Thr Lys Lys Ile Ser Thr Ser Pro Pro Arg
            260                 265                 270
Asp Gly Gly Tyr Phe Leu Ser Ser Asp Ser Gly Trp Lys Thr Asn Phe
            275                 280                 285
Leu Lys Glu Gly Glu Arg His Leu Val Ser Lys Leu Tyr Thr Asp Asp
    290                 295                 300
Met Arg Pro Glu Thr Val Glu Thr Thr Val Thr Thr Ala Gln Glu Thr
305                 310                 315                 320
Lys Arg Gly Arg Ile Gln Thr Lys Lys Glu Val Ser Ile Lys Thr Thr
                325                 330                 335
Leu Lys Glu Leu Val His Lys Arg Val Thr Ser Pro Glu Asp Trp Met
            340                 345                 350
Met Met Gln Pro Asp Ser Tyr Ile Glu Met Met Ala Gln Pro Gly Gly
            355                 360                 365
Glu Asn Leu Leu Lys Asn Thr Leu Glu Ile Cys Thr Leu Thr Leu Ala
    370                 375                 380
Arg Thr Lys Thr Ala Phe Asp Leu Ile Leu Glu Lys Ala Glu Thr Ser
385                 390                 395                 400
Lys Leu Thr Asn Phe Ser Leu Pro Asp Thr Arg Thr Cys Arg Ile Phe
                405                 410                 415
Ala Phe His Gly Trp Asn Tyr Val Lys Val Cys His Ala Ile Cys Cys
            420                 425                 430
Val Leu Asn Arg Gln Gly Gly Lys Arg Asn Thr Val Leu Phe His Gly
            435                 440                 445
Pro Ala Ser Thr Gly Lys Ser Ile Ile Ala Gln Ala Ile Ala Gln Ala
    450                 455                 460
Val Gly Asn Val Gly Cys Tyr Asn Ala Ala Asn Val Asn Phe Pro Phe
465                 470                 475                 480
Asn Asp Cys Thr Asn Lys Asn Leu Ile Trp Val Glu Glu Ala Gly Asn
                485                 490                 495
Phe Gly Gln Gln Val Asn Gln Phe Lys Ala Ile Cys Ser Gly Gln Thr
            500                 505                 510
Ile Arg Ile Asp Gln Lys Gly Lys Gly Ser Lys Gln Ile Glu Pro Thr
    515                 520                 525
Pro Val Ile Met Thr Thr Asn Glu Asn Ile Thr Val Val Arg Ile Gly
    530                 535                 540
Cys Glu Glu Arg Pro Glu His Thr Gln Pro Ile Arg Asp Arg Met Leu
545                 550                 555                 560
Asn Ile His Leu Thr His Thr Leu Pro Gly Asp Phe Gly Leu Val Asp
                565                 570                 575
Lys Asn Glu Trp Pro Met Ile Cys Ala Trp Leu Val Lys Asn Gly Tyr
            580                 585                 590
Gln Ser Thr Met Ala Ser Tyr Cys Ala Lys Trp Gly Lys Val Pro Asp
            595                 600                 605
Trp Ser Glu Asn Trp Ala Glu Pro Lys Val Pro Thr Pro Ile Asn Leu
    610                 615                 620
```

-continued

```
Leu Gly Ser Ala Arg Ser Pro Phe Thr Thr Pro Lys Ser Thr Pro Leu
625                 630                 635                 640

Ser Gln Asn Tyr Ala Leu Thr Pro Leu Ala Ser Asp Leu Glu Asp Leu
            645                 650                 655

Ala Leu Glu Pro Trp Ser Thr Pro Asn Thr Pro Val Ala Gly Thr Ala
        660                 665                 670

Glu Thr Gln Asn Thr Gly Glu Ala Gly Ser Lys Ala Cys Gln Asp Gly
            675                 680                 685

Gln Leu Ser Pro Thr Trp Ser Glu Ile Glu Glu Asp Leu Arg Ala Cys
        690                 695                 700

Phe Gly Ala Glu Pro Leu Lys Lys Asp Phe Ser Glu Pro Leu Asn Leu
705                 710                 715                 720

Asp

<210> SEQ ID NO 17
<211> LENGTH: 672
<212> TYPE: PRT
<213> ORGANISM: Porcine parvovirus 7

<400> SEQUENCE: 17

Met Glu His Pro Gly Ser Arg Arg Glu Arg Lys Leu Glu Arg Trp Arg
1               5                   10                  15

Trp Ile Gly Asn Thr Val Val Gln Glu Thr Ala Pro Leu Glu Ser Val
            20                  25                  30

Ala Leu Thr Pro Glu Gln Leu Glu Val Ala Lys Ala His Leu Asn Met
        35                  40                  45

Gln Gln Trp Gln Gly Met Val Met Met Leu Ser Asn Gly Glu Gly Arg
    50                  55                  60

Pro Arg Thr Gln Pro Asp Ile Arg Ala Ile Ala Phe Leu Leu Ser Gln
65                  70                  75                  80

Leu Lys Thr Val Arg Asp Trp Cys Phe Val Ala Glu Thr Asn Thr Asp
                85                  90                  95

Gly Ile Leu His Tyr His Cys Leu Val Lys Thr Ser Gln Arg Ser Asp
            100                 105                 110

Ala Leu Arg Asp Ser Val His Arg Arg Trp Glu Gln Cys Lys Leu Ala
        115                 120                 125

Ala Met Glu Asp Ile Glu Glu Pro Asp Pro Gln Ile Glu Val Leu Lys
    130                 135                 140

Ser Gln Lys Ala His Arg Pro Gly Ser Leu Met Glu Tyr Met Met Lys
145                 150                 155                 160

Gly Pro Leu Cys Phe Cys Ala Tyr Ser Asp Thr Thr Met Ala Leu Gly
                165                 170                 175

Ala Ser Ile Tyr Leu Tyr Asn Gln Gly Gln Arg Phe Ala Glu Lys Glu
            180                 185                 190

Lys Gln Lys Gln Lys Arg Lys Gln Ile Leu Gly Pro Glu Val Leu Gln
        195                 200                 205

Gly Ala His Ser Leu Thr Arg Asp Leu Leu Gly Val Ile Tyr Thr Tyr
    210                 215                 220

Asn Cys Gln Ser Ala Glu Asp Ile Phe Arg Asn Ala Pro Asp Leu Val
225                 230                 235                 240

Val Ala His Leu His Lys Pro Gly Phe Gln Gln Ile Val Lys Asn Cys
                245                 250                 255

Leu Gly Phe Val Asp Ala Thr Lys Asp Asn Trp Ser Met Gln Asp Asn
            260                 265                 270
```

```
Ala Arg Arg Thr Pro Pro Asp Pro Thr Ala Ile His Thr Cys Leu Ala
            275                 280                 285

His Gln Gly Leu Asp Ile Asp Asn Phe Asp Ala Thr Met Tyr Ala Trp
    290                 295                 300

Ile Thr Lys Lys Ser Asp Lys Arg Asn Thr Ile Val Leu Trp Gly Pro
305                 310                 315                 320

Ser Asn Thr Gly Lys Thr Ala Phe Ile Arg Gly Leu Arg Gln Val Val
                325                 330                 335

Asn Cys Gly Glu Cys Cys Asn Gly Gln Ile Phe Cys Phe Glu Gly Leu
                340                 345                 350

Cys Gly Lys Ala Ile Gly Ile Trp Glu Glu Pro Leu Ile Ser Pro Glu
            355                 360                 365

Cys Ala Glu Lys Ala Lys Gln Ile Phe Glu Gly Ala Asp Thr Gln Val
        370                 375                 380

Pro Ala Lys Tyr Lys Lys Pro Gln Asp Leu Pro Arg Thr Pro Ile Ile
385                 390                 395                 400

Met Thr Thr Asn His Ala Pro Trp Arg Phe Cys Thr Ser Glu Glu Gly
                405                 410                 415

Ala Leu Arg Asn Arg Met Phe Ile Phe Ile Trp Asp Lys Asp Cys Thr
                420                 425                 430

Asp Gly Val Phe Val Arg Arg Ser Gly Ser Cys Cys Gln Cys Arg
            435                 440                 445

Gly Cys Gln Gly Cys Gly Gly Glu Val Pro Ala Gln Gln Arg Gly
        450                 455                 460

Ala Gly Gln Val Pro Gly Gln Gln Ser Leu Gln Pro Val Gly Ala
465                 470                 475                 480

Arg Leu Pro Gly Ser Gly Ala Asp Val Gly Gly Cys Ser Gly Pro
                485                 490                 495

Val Ser Gly Gly Leu Glu Ser Gly Asp Glu Arg Leu Leu Cys Thr Ser
                500                 505                 510

Glu Cys Gly Glu Asp Leu Ser Trp Ser Asp Asp Leu His Arg Arg
                515                 520                 525

Cys Ala Ser Val Ser Thr Leu Glu Cys Ala Glu Leu Ala Arg Leu Gly
        530                 535                 540

Phe Ser Thr Gly Thr Ala Ala Gly Asp Glu Trp Gly Ser Gly Gly Asp
545                 550                 555                 560

His Gly Ser Gly Tyr Pro Asn Leu Arg Val Tyr Ser Ala Gly Gly Gly
                565                 570                 575

Asp Gly Val Leu Val Glu Pro Glu Gln His Arg Gly Gly Asp Gly Ala
                580                 585                 590

Asp Pro Gly Gly Asp Gly Gly Ala Ile Gly Ala Ile Thr Gly Gly
            595                 600                 605

Pro Gly Gly Asp Arg Glu Gln His Ala Arg Gly Gly Asp Val Val Val
        610                 615                 620

Leu Glu Gln Gly Ser Gln His Gly His Gln Met Ala Ser Glu Glu Ser
625                 630                 635                 640

Gly Val Gly Gly Glu Val Asp Pro Val Met Val Ile Pro Thr Lys Gln
                645                 650                 655

His Trp Cys Ala Tyr Leu Ser Tyr Leu Glu His Cys Phe Gly Asp Gln
            660                 665                 670

<210> SEQ ID NO 18
<211> LENGTH: 654
<212> TYPE: PRT
```

<213> ORGANISM: Rat parvovirus 2

<400> SEQUENCE: 18

Met Gln Ala Lys Met Glu Cys Thr Arg Arg Gly Leu Thr Ala Ala Arg
1               5                   10                  15

Arg Tyr Phe Trp His Lys Gly Ser Ala Val Glu Thr Thr Glu Val Ser
            20                  25                  30

Ile Glu Asp Asp Thr Leu Thr Arg Thr Leu Arg Thr Trp Asp Ser Gly
        35                  40                  45

Thr Trp Lys Ala Ala Ile Leu Gln Ile Ser Cys Leu Gly Lys Pro Pro
50                  55                  60

Val Glu Glu Pro Glu Pro Tyr Ala Phe Leu Leu Asn Glu Met Pro Met
65                  70                  75                  80

Asn Thr Asp Trp Ile Ala Thr Gly Glu Ala Asn Ser Asp Gly Ile Phe
                85                  90                  95

His Val His Ala Leu Val Arg Asn Pro Gln Arg Thr Asp Ala Trp Ile
            100                 105                 110

Arg Ser Ala Asn Ser Lys Trp Phe Ser Val Arg Cys Ala Thr Leu Asn
        115                 120                 125

Asp Val Glu Asp Thr Asp Pro Met Leu Thr Ile Leu Lys Cys Gln Thr
    130                 135                 140

Ala His Lys Pro Ser Ser Leu Ala Cys Tyr Met Val Lys Asn Pro Val
145                 150                 155                 160

Trp Leu Ile Ala Ser Ser Ala Phe Asn Leu Lys Val Leu Ser Gly Leu
                165                 170                 175

His Asp Arg Asp Met Gly Asp Arg Phe Arg Pro Glu Asn Ser Arg Lys
            180                 185                 190

Leu Lys Leu Asp Ala Asn Lys Met Thr Thr Asp Leu Ile Asp Ile Ile
        195                 200                 205

Ser Asp His Asn Cys Lys Thr Pro Gln Asp Val Phe Arg Cys Ala Pro
    210                 215                 220

Glu Val Ile Val Gln Tyr Leu His Arg Pro Gly Phe Gly Ser Ile Leu
225                 230                 235                 240

Asn Asn Cys Leu Ala Trp Val Gln Ala Thr Gln Gly Gly Trp Ser Met
                245                 250                 255

Ala Asn Ile Ala Lys Lys His Lys Pro Met Pro Thr Arg Val His Gln
            260                 265                 270

Val Leu Leu His Gln Gly Ile Ile Pro Ser Glu Phe Asp Glu Ile Phe
        275                 280                 285

Tyr Lys Trp Ile Thr Lys Ala Glu Ser Lys Arg Asn Thr Leu Val Leu
    290                 295                 300

Trp Gly Pro Ser Asn Thr Gly Lys Ser Met Phe Ile Lys Gly Phe Lys
305                 310                 315                 320

Glu Ala Val Pro Trp Gly Glu Ile Val Asn Ser Asn Gln Phe Ala Phe
                325                 330                 335

Glu Ser Leu Cys Glu Ser Met Phe Gly Val Trp Glu Pro Leu Ile
            340                 345                 350

Ser Ser Glu Gln Ala Glu Lys Cys Lys Gln Ile Phe Glu Gly Met Glu
        355                 360                 365

Thr Ser Val Pro Val Lys Tyr Lys Lys Pro Phe Lys Leu Pro Arg Ile
    370                 375                 380

Pro Ile Ile Met Thr Thr Asn His Ala Pro Trp Arg Tyr Cys Ser Asn
385                 390                 395                 400

Glu Glu Pro Met Phe Arg Asn Arg Met Trp Ile Phe Glu Trp Leu Asn
            405                 410                 415

Asp Cys Thr Gly Leu Tyr Ser Cys Arg Ala Ser Glu His Ser Cys Glu
            420                 425                 430

Cys Cys Val Cys Lys Ala Ser Arg Ser Gly Lys Gly Ile Asn Asp Gly
            435                 440                 445

Gln Ser Ala Cys Lys Met Pro Arg Gly Gln Pro Val Gln Gly Leu
    450                 455                 460

Ala Phe Trp Ile Gly Ser Thr Glu Asp Val Ser Thr Gly Ser Leu
465                 470                 475                 480

Cys Ser Gly Ser Gln Gly Ser Cys Arg Ser Pro Glu Arg Gly Asp Cys
            485                 490                 495

Glu Arg Ser Thr Ser Pro Thr Ser Gln Cys Gln Gln Cys Ser Asn
            500                 505                 510

Ser Ser Gly Ser Ser Ser Ser Ser Ser Thr Val Asp Ser Leu
            515                 520                 525

Arg Ser Ser Gly Glu His Arg Pro Ser Asn Pro Arg Lys Arg Ile Arg
    530                 535                 540

Ser Ser Glu Ser Gly Asp Ala Glu Pro Met Val Thr Glu Gln Ser Gly
545                 550                 555                 560

Gly Asp His Gly Gly Asp Leu Gly Arg His Gly Met Gly Glu Asp Gly
            565                 570                 575

Gly Asp His Ala Ser Gly Ser His Glu Asp Ser Gly Arg Gly Gly
            580                 585                 590

Glu Leu Pro Ser Ser Ser Met Val Val Leu Gly Thr Ser Asn
    595                 600                 605

Thr Leu Thr Pro Leu Glu Ile Leu Thr Ala Glu Arg Glu Leu Asp Arg
    610                 615                 620

Lys Val Gly Ala Leu Ser Ile Pro Thr Arg Asn Asp Trp Leu Cys Tyr
625                 630                 635                 640

Leu Ser Phe Leu Gln Thr Thr Tyr Ala Asn Lys Cys Asn Leu
            645                 650

<210> SEQ ID NO 19
<211> LENGTH: 441
<212> TYPE: PRT
<213> ORGANISM: Eidolon helvum parvovirus 2

<400> SEQUENCE: 19

Met Gln Ala Gln Met Glu Gly Thr Arg Arg Ser Leu His Asp Ile Arg
1               5                   10                  15

Arg Tyr Trp Trp Thr Gly Ser Ala Val Leu Glu Gln Arg Glu Asn Gln
            20                  25                  30

Glu Ile Ile Pro Tyr Gln Gln Leu Gln Thr Ile Leu His Thr Trp Asp
        35                  40                  45

Ser Arg Val Trp Gln Ala Cys Val Leu Ser Ile Trp Asp Thr Thr Ala
    50                  55                  60

Thr Ser Asp Pro Arg Pro Tyr Cys Phe Leu Ile Asp Asn Ile Lys Ser
65                  70                  75                  80

Val Lys Ala Trp Leu Leu Ser Ala Glu Leu Asp Ser Asn Ala Gln Pro
                85                  90                  95

His Val His Leu Leu Ala Leu Thr His Gln Arg Ser Asp Ala Phe Lys
            100                 105                 110

Arg Ser Leu Glu Gln Ser Trp Pro Asn Val Arg Phe Ile Ala Leu Ser
        115                 120                 125

-continued

```
Asp Leu Glu Gln Pro Asp Pro Thr Leu Glu Val Val Lys Cys Gln Lys
    130                 135                 140
Cys His Lys Pro Ser Ser Leu Ile Ala Tyr Met Thr Lys Asp Pro Leu
145                 150                 155                 160
Trp Leu Ala Cys Arg Ser Glu Thr Asp Leu Val Val Phe Gln Ser Val
                165                 170                 175
Tyr Ala Tyr Asp Leu Gly Glu Arg Phe Arg Leu Arg Gln Gln Gln Glu
            180                 185                 190
Gln Ala Arg Lys Ala Asp Pro Ser Thr Ala Gly Met Asn Ala Leu Thr
        195                 200                 205
Ala Glu Ile Thr Asp Val Ile Met Gln His Asn Cys Lys Ser Ile Glu
    210                 215                 220
Asp Cys Met Lys Ser Ala Pro Glu Ile Ile Ala Lys His Leu His Arg
225                 230                 235                 240
Ser Gly Ile Ala Thr Ile Ile Gln Asn Cys Ile Thr Trp Val Thr Ser
                245                 250                 255
Thr Gly Gly Gly Trp Ser Leu Ser Lys Ile Gly Ala Arg His Ser Pro
            260                 265                 270
Asp Pro Ala Val Ile His Thr Val Leu Leu His Gln Gly Ile Glu Pro
        275                 280                 285
Ser His Phe Asp Ser His Phe Tyr Trp Trp Val Thr Lys Gln Thr Asp
    290                 295                 300
Lys Lys Asn Thr Phe Val Leu Trp Gly Pro Ser Asn Thr Gly Lys Ser
305                 310                 315                 320
Met Phe Ile His Gly Phe Lys Gln Cys Val Asn Trp Gly Glu Val Val
                325                 330                 335
Asn Ser Asn Thr Phe Ala Phe Glu Gly Leu Ile Asn Asn Gln Phe Gly
            340                 345                 350
Ile Trp Glu Glu Pro Leu Ile Ser Pro Glu Leu Ala Glu Lys Ala Lys
        355                 360                 365
Gln Ile Phe Glu Gly Met Glu Thr Ser Ile Pro Val Lys Tyr Arg Lys
    370                 375                 380
Pro Val Lys Leu Pro Arg Thr Pro Ile Leu Met Thr Thr Asn His Ala
385                 390                 395                 400
Pro Trp Arg Phe Cys Thr Lys Glu Glu Asp Met Phe Arg Asn Arg Met
                405                 410                 415
Ile Ile Phe Glu Trp Asn Glu Thr Thr Tyr Asn Val Pro Phe Thr Cys
            420                 425                 430
Arg Val Ser Glu Tyr Ser Cys Lys Cys
        435                 440
```